Figure 1:
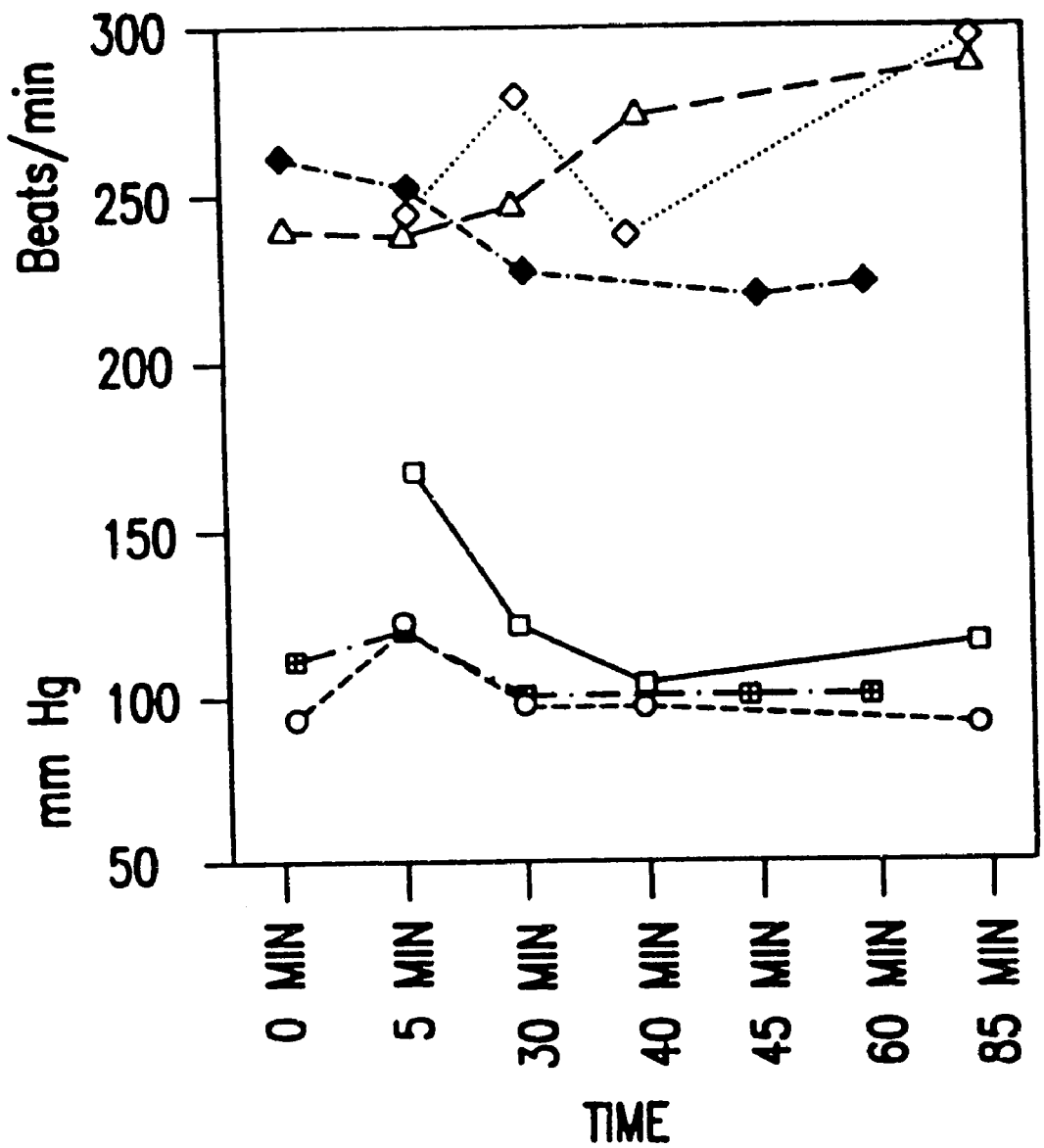

United States Patent [19]
Dewhirst et al.

[11] Patent Number: 6,020,308
[45] Date of Patent: Feb. 1, 2000

[54] METHODS FOR IMPROVING THERAPEUTIC EFFECTIVENESS OF TREATMENT OF VASCULARIZATION DISORDERS

[75] Inventors: Mark W. Dewhirst, Chapel Hill; Robert E. Meyer, Cary; Joseph Bonaventura, Beaufort, all of N.C.; Joseph DeAngelo, Hamtramck, Mich.

[73] Assignees: Duke University, Durham; North Carolina State University, Raleigh; Apex Bioscience, Inc., Durham, all of N.C.

[21] Appl. No.: 09/126,930

[22] Filed: Jul. 31, 1998

Related U.S. Application Data

[62] Division of application No. 08/709,938, Sep. 6, 1996, Pat. No. 5,788,958, which is a division of application No. 08/246,882, May 20, 1994, Pat. No. 5,554,638, which is a continuation-in-part of application No. 08/066,756, May 24, 1993, Pat. No. 5,612,310.

[51] Int. Cl.[7] .......................... A61K 38/16; A61K 35/14
[52] U.S. Cl. ................. 514/6; 514/12; 514/561; 514/565; 514/832; 514/833; 514/929; 514/930; 530/385
[58] Field of Search ................ 514/6, 561, 565, 514/121, 832, 833, 929, 930; 530/385

[56] References Cited

U.S. PATENT DOCUMENTS

| | | |
|---|---|---|
| 4,001,401 | 1/1977 | Bonsen et al. |
| 4,061,736 | 12/1977 | Morris et al. |
| 4,301,144 | 11/1981 | Iwashita |
| 4,321,259 | 3/1982 | Nicolau |
| 4,377,512 | 3/1983 | Ajisaka |
| 4,412,989 | 11/1983 | Iwashita |
| 4,473,563 | 9/1984 | Nicolau |
| 4,584,130 | 4/1986 | Bucci et al. |
| 4,598,064 | 7/1986 | Walder |
| 4,650,786 | 3/1987 | Wong |
| 4,670,417 | 6/1987 | Iwasaki |
| 4,710,488 | 12/1987 | Wong |
| 4,812,449 | 3/1989 | Rideout |
| 5,028,588 | 7/1991 | Hoffman et al. |
| 5,266,594 | 11/1993 | Dawson et al. |
| 5,273,875 | 12/1993 | Griffith |
| 5,295,944 | 3/1994 | Teicher et al. |
| 5,296,466 | 3/1994 | Kilbourn et al. |
| 5,298,490 | 3/1994 | Heavner et al. |
| 5,298,506 | 3/1994 | Stamler et al. |
| 5,312,835 | 5/1994 | Kilbourn et al. |
| 5,317,040 | 5/1994 | Goldman |
| 5,334,380 | 8/1994 | Kilbourn et al. |

FOREIGN PATENT DOCUMENTS

| | | |
|---|---|---|
| WO 88/03408 | 5/1988 | WIPO |
| WO 90/13645 | 11/1990 | WIPO |
| WO 93/08831 | 5/1993 | WIPO |

OTHER PUBLICATIONS

Andrade et al., 1992, "Inhibitors of nitric oxide synthase selectively reduce flow in tumour–associated neovasculature", *Br. J. Pharmacol.* 107:1092–1095.

Babbs & DeWitt, 1981, "Physical Principles of local heat therapy for cancer", *Med. Instrum.* 15:367–373.

Botstein & Shortle, 1985, "Strategies and applications of in vitro mutagenesis", *Science* 229:1193–1201.

Brizel et al., 1994, *Int. J. Radiation Oncol. Biol. Phys.* 30:635–642.

Brown & Koong, 1991, "Therapeutic advantage of hypoxic cells in tumors: a theoretical study", *J. Natl. Cancer Inst.* 83:178–185.

Caruthers et al., 1982, "New methods for synthesizing deoxyoligonucleotides", *Genetic Engineering*, Setlow & Hollaender eds., Plenum Press, NY, 4:1–17.

Chapman et al., 1987, "Keynote address: cellular reduction of nitroimidazole drugs: potential for selective chemotherapy and diagnosis of hypoxic cells", *Int. J. Rad. Oncol. Biol. Phys.* 16:911–917.

Chen et al., 1981, "Microvascular rarefaction in spontaneously hypertensive rat cremaster muscle", *Am. J. Physiol.* 241:H306–H310.

Collman et al., 1975, "'Picket fence porphyrins.' Synthetic models for oxygen binding proteins", *J. Am. Chem. Soc.* 97:1427–1439.

W.A. Denny, 1995, "Bioreductive Drugs: A unique opportunity for de novo design", *Ninth Intl. Conf. on Chem. Modifier of Cancer Treatment*, abstr. p. 33.

De Venuto et al., 1979, "Appraisal of hemoglobin solution as a blood substitute", *Surgery Gynecol. and Obstetr.* 149:417–436.

Dewhirst et al., 1990, "The use of hydralazine to manipulate tumour temperatures during hyperthermia", *Int. J. Hyperthermia* 6:971–983.

Feola et al., 1983, "Development of a bovine stroma–free hemoglobin solution as a blood substitute", *Surgery Gynecol. and Obstetr.* 157:399–408.

Fishman et al., 1985, *Medicine* 2d Ed., J.B. Lippincott Co., Philadel., PA.

Froehler, 1986, "Synthesis of DNA via deoxynucleotide H–phosphonate intermediates", *Nucl. Acids Res.* 14:5399–5407.

Gatenby et al., 1988, "Oxygen distribution in squamous cell carcinoma metastases and its relationship to outcome of radiation therapy", *Int. J. Radiation Oncology Biol. Phys.* 14:831–838.

Hahn & Shiu, 1985, "Protein synthesis, thermotolerance and step down heating", *Int. J. Radiat. Oncol. Biol. Phys.* 11:159–164.

Hilf et al., 1965, "Biochemical and morphologic properties of a new lactating mammary tumor line in the rat", *Cancer Res.* 25:286–299.

(List continued on next page.)

Primary Examiner—Michael P. Woodward
Assistant Examiner—Abdel A. Mohamed
Attorney, Agent, or Firm—Pennie & Edmonds LLP

[57] ABSTRACT

The present invention is directed to the use of an inhibitor of NO activity, such as a nitric oxide scavenger or an NO synthase inhibitor, as as an adjunct to treatment of inappropriate tissue vascularization disorders.

8 Claims, 14 Drawing Sheets

OTHER PUBLICATIONS

Höckel et al., 1993, "Intratumoral pO$_2$ predicts survival in advanced cancer of the uterine cervix", *Ratiother. and Oncol.* 26:45–50.

Hunkapilar et al., 1984, "A microbial facility for the analysis and synthesis of genes and proteins", *Nature (London)* 310:105–111.

R.K. Jain, 1988, "Determinants of tumor blood flow: a review", *Cancer Res.* 48:2641–2658, 1988.

R.K. Jain, 1989, "Delivery of novel therapeutic agents in tumors: Physiological barriers and strategies", *J. Natl. Cancer Inst..* 81:570–576.

Jones & Howard, 1990, "A rapid method for site–specific mutagenesis and directional subcloning by using the polymerase chain reaction to generate recombinant circles", *Biotechniques* 8:178–180.

Karuri et al., 1993, "Selective cellular acidification and toxicity of weak organic acids in an acidic microenvironment", *Br. J. Cancer* 68:1080–1087.

Kavanagh et al., 1993, "The effect of flunarizine on erythrocyte suspension viscosity under conditions of extreme hypoxia, pH, and lactate treatment", *Br. J. Cancer* 67:734–741.

Kilbourne et al., 1990, "N$^G$–Methyl–L–arginine inhibits tumor necrosis factor–induced hypotension: implications for the involvement of nitric oxide", *PNAS USA* 87:3629–3832.

Labossiere et al., 1972, "Hemoglobin Deer Lodge: $\alpha_2\beta_2$ $^{2\ His \rightarrow Arg}$ ", *Clin. Biochem.* 5:46–50.

Less et al., 1992, "Interstitial hypertension in human breast and colorectal tumors", *Cancer Res.* 52:6371–6374.

Leunig et al., 1992, "Angiogenesis, microvascular architecture, microhemodynamics, and interstitial fluid pressure during early growth of human adenocarcinoma LS174T in SCID mice", *Cancer Res.* 52:6553–6560.

Maeda et al., 1994, "Enhanced vascular permeability in solid tumor is mediated by nitric oxide and inhibited by both new nitric oxide scavenger and nitric oxide synthase inhibitor", *Jpn. J. Cancer Res.* 85:331–334.

Martin et al., 1986, "The mechanisms by which haemoglobin inhibits the relaxation of rabbit aorta induced by nitrovasodilators, nitric oxide, or bovine retractor penis inhibitory factor", *Br. J. Pharmacol.* 89:563–571.

Martin et al., 1993, "Changes in the oxygenation of head and neck tumors during carbogen breathing", *Radiother. and Oncol.* 27:123–130.

McCormick & Atorssi, 1990, "Hemoglobin binding with haptoglobin: delineation of the haptoglobin binding site on the α–chain of human hemoglobin", *J. Prot. Chem.* 9:735.

Merrifield, 1963, "Solid phase peptide synthesis. I. The synthesis of a tetrapeptide", *J. Chem. Soc.* 85:2149–2154.

Meyer et al., 1995, "Nitric oxide synthase inhibition irreversibly decreases perfusion in the R3230Ac rat mammary adenocarcinoma", *Br. J. of Cancer* 71:1169–1174.

Moncada et al., 1991, "Nitric Oxide: physiology, pathophysiology, and pharmacology", *Pharm. Rev.* 43:109–142.

Papenfuss et al., 1979, "A transparent access chamber for the rat dorsal skin fold", *Microvascular Res.* 18:311–318.

Perutz, 1974, "Mechanism of denaturation of haemoglobin by alkali", *Nature* 247:341.

Prescott et al., 1990, "Use of Nitroprusside to increase tissue temperature during local hyperthermia in normal and tumor–bearing dogs", *Int. J. Hyperthermia* 23:377–385.

Radomski et al., 1991, "Human colorectal adenocarcinoma cells: differential nitric oxice synthesis determines their ability to aggregate platelets", *Cancer Res.* 51:6073–6078.

Ramsay et al., 1992, "Phase I study of BW12C in combination with mitomycin C in patients with advanced gastrointestinal cancer", *Int. J. Radiation Oncol. Biol. Phys.* 22:721–725.

*Remington's Pharmaceutical Sciences*, Gennaro et al., eds., Mack Pub. Co., Easton, PA, latest ed.

Robbins & Angell, 1976, *Basic Pathology*, 2d Ed., W.B. Saunders Co., Philadel., PA, pp. 68–79.

Roh et al., 1991, "Interstitial hypertension in carcinoma of uterine cervix in patients: Possible correlation with tumor oxygenation and radiation response", *Cancer Res.* 51:6695–6698.

Sehgal et al., 1984, "Polymerized pyrodoxylated hemoglobin: a red cell substitute with normal oxygen capacity", *Surgery* 95:433–438.

Sevick & Jain, 1989, "Geometric resistance to blood flow in solid tumors perfused ex vivo: effects of tumor size and perfusion pressure", *Cancer Res.* 49:3506–3512.

Tentori et al., 1972, "Hemoglobin Abruzzo: β 143 (H21) His → Arg", *Clin. Chim. Acta* 38:158–262.

Tompkins et al., 1974, "Velocity measurement by self–tracking correlator", *Rev. Sci. Instrum.* 45:647–649.

Tozer et al., 1995, "The influence of nitric oxide on tumour vascular tone", *Acta Oncologica* 34:373–377.

Traylor & Traylor, 1982, "Considerations for the design of useful synthetic oxygen carriers", *Ann. Rev. Biophys. Bioeng.* 11:105–127.

Vaupel et al., 1989, "Blood flow, oxygen and nutrient supply, and metabolic microenvironment of human tumors: A review", *Cancer Res.* 49:6449–6465.

Wilson et al., 1995, "NSC 654891, a new dinitrobenzamide mustard designed to combine selectivity for both hypoxia and acidosis in tumours", *Ninth Intl. Conf. on Chem. Modifier of Cancer Treatment* abstr. p. 63.

Winslow et al., 1976, "Hemoglobin McKees Rocks ($\alpha_2\beta_2$ $^{145\ Tyr \rightarrow Term}$", *J. Clin. Invest.* 57:772–781.

Wood et al., 1993, "Changes in tumour phosphorus metabolism by the nitric oxide donor sin–1", abstract presented at 41st Ann. Mtg. of Radiation Res. Soc., Dallas, TX, Mar. 20–25.

Wood et al., 1993, "Modification of energy metabolism and radiation response of a murine tumour by changes in nitric oxide availability", *Biochem. and Biophys. Res. Comm.* 192:505–510.

Wood et al., 1994, "Modification of metabolism of transplantable and spontaneous murine tumors by the nitric oxide synthase inhibitor, Nitro–L–Arginine", *Int. J. Radiation Oncol. Biol. Phys.* 29:443–447.

Wood et al., 1994, "Induction of hypoxia in experimental murine tumors by the nitric oxide synthase inhibitor, N$^G$–Nitro–L–arginine", *Cancer Res.* 54:6458–6463.

Wood et al., 1994, "The NO synthase inhibitor nitro–L–arginine alters tumor metabolism, and response to X–rays and bioreductive drugs", 42nd Ann. Mtg. of Radiation Res. Soc. and the 14th Ann. Mtg., North American Hyperthermia Soc., Apr. 29–May 4, Nashville, TN.

Zoller & Smith, 1984, "Oligonucleotide–directed mutagenesis: a simple method using two oligonucleotide primers and a single –stranded DNA template", *DNA* 3:479–488.

METHODS FOR IMPROVING THERAPEUTIC EFFECTIVENESS OF TREATMENT OF VASCULARIZATION DISORDERS

The present application is a divisional of application Ser. No. 08/709,938 filed Sep. 6, 1996, now U.S. Pat. No. 5,788,958 which is a divisional of application Ser. No. 08/246,882 filed May 20, 1994, U.S. Pat. No. 5,554,638, which is a continuation-in-part of application Ser. No. 08/066,756 filed May 24, 1993, U.S. Pat. No. 5,612,310, each of which is incorporated herein by reference in its entirety.

TABLE OF CONTENTS

1. FIELD OF THE INVENTION
2. BACKGROUND OF THE INVENTION
   2.1. HYPOXIC AND HYPERTHERMIC TUMOR THERAPY
   2.2. NITRIC OXIDE (NO)
3. SUMMARY OF THE INVENTION
4. DESCRIPTION OF THE FIGURES
5. DETAILED DESCRIPTION OF THE INVENTION
   5.1. NO SCAVENGERS
   5.2. INHIBITORS OF NO SYNTHESIS
      5.2.1. OTHER INHIBITORS OF NO ACTIVITY
      5.2.2. REVERSAL OF NO SYNTHESIS INHIBITION IN NORMAL TISSUE
   5.3. THERAPEUTIC METHODS AND COMPOSITIONS
      5.3.1. ADMINISTRATION OF INHIBITORS OF NO ACTIVITY
      5.3.2. ADMINISTRATION WITH HYPOXIC AND ACIDIC CYTOTOXINS
      5.3.3. ADMINISTRATION WITH HYPERTHERMIA
      5.3.4. SOLID TUMORS
      5.3.5. IRREVERSIBLE REDUCTION IN TUMOR PERFUSION
6. PHARMACOLOGICAL REDUCTION OF TUMOR PERFUSION: A MECHANISM TO IMPROVE THERAPEUTIC EFFECTIVENESS OF BIOREDUCTIVE CHEMOTHERAPEUTIC AGENTS AND HYPERTHERMIA
   6.1. METHODS
      6.1.1. GENERAL EXPERIMENTAL PROCEDURE
      6.1.2. NO SYNTHASE INHIBITION EXPERIMENTS
      6.1.3. NO SCAVENGING EXPERIMENTS
      6.1.4. NO SCAVENGING HYPOXIC SENSITIZER EXPERIMENTS
   6.2. RESULTS
      6.2.1. NO SYNTHASE EXPERIMENTS SUPERFUSION
      6.2.2. NO SYNTHASE INHIBITION EXPERIMENTS INTRAVENOUS ADMINISTRATION
      6.2.3. NO SCAVENGING EXPERIMENTS
      6.2.4. NO SCAVENGING HYPOXIC SENSITIZER EXPERIMENTS
   6.3. CONCLUSIONS
7. EXAMPLE: CHANGES IN TISSUE AND TUMOR OXYGENATION WITH ADMINISTRATION OF STROMA FREE HEMOGLOBINS
   7.1. MATERIALS AND METHODS
   7.2. RESULTS
   7.3. DISCUSSION
8. SELECTIVE REDUCTION OF TUMOR PERFUSION WITH NITRIC OXIDE SYNTHASE INHIBITION
   8.1. MATERIALS AND METHODS
      8.1.1. ANIMAL MODEL
      8.1.2. MEASUREMENT OF VENULE INTRALUMINAL DIAMETER AND RBC VELOCITY
      8.1.3. DETERMINATION OF VESSEL LENGTH DENSITY AND INTERMITTENT FLOW RATIO
      8.1.4. EXPERIMENTAL PROTOCOL
      8.1.5. STATISTICAL ANALYSIS
   8.2. RESULTS
      8.2.1. BASELINE PARAMETERS
      8.2.2. VESSEL DIAMETER
      8.2.3. RBC VELOCITY
      8.2.4. VENULE FLOW
      8.2.5. VESSEL LENGTH DENSITY
      8.2.6. INTERMITTENT VASCULAR FLOW AND STASIS
   8.3. CONCLUSIONS

1. FIELD OF THE INVENTION

The present invention is directed to administration of a nitric oxide (NO) scavenger or an NO synthesis inhibitor as an antitumor therapy to reduce tumor blood flow and oxygenation or as an adjunct therapy to enhance the effectiveness of tumor therapy with hypoxic or acidic chemotherapeutic agents or hyperthermia. The invention is also directed to the administration of an NO synthase substrate subsequent to the administration of an NO synthase inhibitor, in order to reverse the effect of the inhibitor on normal tissue.

2. BACKGROUND OF THE INVENTION

2.1. Hypoxic and Hyperthermic Tumor Therapy

A relatively new and novel approach to solid tumor therapy has involved the induction of tumor hypoxia following the administration of drugs that are selectively cytotoxic to hypoxic cells (Chaplin and Acker, 1987, Int. J. Rad. Oncology, Biol. Phys. 16:911–917; Brown and Koong, 1991, J. Natl. Cancer Inst. 83:178–185). The strategy typically involves the systemic administration of a hypoxic cell cytotoxin, followed by the administration of a drug that selectively reduces tumor blood flow. The reduction in tumor blood flow traps the cytotoxic agent within the tumor mass and increases its cytotoxicity via induction of hypoxia (Babbs and DeWitt, 1981, Med. Instrum. 15:367–373; Chaplin and Acker, 1987, Int. J. Rad. Oncology, Biol. Phys. 16:911–917; Jain, 1988, Cancer Res. 48:2641–2658; Dewhirst et al., 1990, Int. J. Hyperthermia 6:971–983).

Hyperthermia adjunct therapy for tumors is an area of active investigation. An improvement in achievement of elevated temperatures has been seen with reduction in tumor blood flow with vasodilators (Dewhirst, et al., 1990, Int. J. Hyperthermia 6:971–983). Acidosis of tumors also leads to substantial sensitization to heat killing (G. M. Hahn and E. C. Shiu, Int. J. Radiat. Oncol. Biol Phys., 11:159–164, 1985).

Previous efforts to reduce tumor blood flow have focused primarily on vasodilating agents such as hydralazine or nitroprusside. It has been shown that reduction of systemic blood pressure leads to a decrease in tumor blood flow while perfusion of normal tissues either increases or is unaffected. The effects of these agents on normal tissue perfusion is due to organ selectivity in the direct effect of the drugs on arteriolar or venous tone as well as systemic effects on cardiac output and arterial blood pressure. The reduction in tumor perfusion is thought to be the result of vascular collapse in tumors due to high interstitial fluid pressure and high flow resistance in the presence of lowered arterial blood pressure (Sevick and Jain, 1989, Cancer Res. 49:3506–3512). The strategy has been shown to work effectively in murine systems and in tumor bearing dogs (Dewhirst et al., 1990, Int. J. Hyperthermia 6:971–983; Prescott et al., 1990, Int. J. Hyperthermia 23:377–385), but is directly related to the drop in blood pressure. However, the blood pressure decrease required to observe reduced tumor perfusion, to about 60% of normal blood pressure, makes the approach relatively infeasible for clinical application. Such a decrease in blood pressure is especially dangerous for elderly or weak patients. The degree of reduction in systemic blood pressure that is safe in patients is not enough to see an appreciable drop in tumor blood flow.

2.2. Nitric Oxide (NO)

Nitric oxide (NO) is generally regarded as a radical, although the chemical nature of NO remains an area of investigation. NO has recently been identified as an endothelial relaxant factor. It binds to guanylate cyclase in vascular smooth muscle and thereby promotes vasodilation. Inhibition of NO synthase with $N^G$ monomethyl L-arginine (L-NMA) or scavenging of NO with heme proteins causes vasoconstriction and hypertension (Martin et al., 1986, Br. J. Pharmacol. 89:563–571; Moncada et al., 1991, Pharm. Rev. 43:109–142). Platelet aggregation is also decreased by NO (Radomski et al., 1991, Cancer Res. 51:6073–6078). NO is involved in neurotransmission in the central and peripheral nervous system (Moncada et al., 1991, Pharmacol. Rev. 43:109–142.

Inhibitors of NO synthesis, such as $N^G$-nitro-L-arginine and $N^G$-monomethyl-L-arginine have recently been shown to reduce tumor blood flow (Andrade et al., 1992, Br. J. Pharmacol. 107:1092–1095; Wood et al, abstract presented at 41st Ann. Meeting of Radiation Research Society, Dallas, Tex., Mar. 20–25, 1993; Wood et al., abstract presented at 42nd Ann. Meeting of Radiation Research Society, Nashville, Tenn., Apr. 29–May 5, 1994) this effect could be prevented by prior injection of L-arginine (Andrade et al., supra.), a precursor in the synthesis of NO. The NO synthase inhibitor L-NMA was found to increase tumor resistance to X-rays (Wood et al., supra).

Citation or identification of any reference herein shall not be construed as an admission that such reference is available as prior art to the present invention.

3. SUMMARY OF THE INVENTION

The present invention is directed to a method for treating a subject having a solid tumor comprising administering to the subject an amount of an inhibitor of vascular nitric oxide activity, such as a nitric oxide scavenger or a nitric oxide synthase inhibitor, sufficient to decrease tumor blood flow or oxygenation. In another aspect, the invention is directed to a method for treating a subject having a solid tumor comprising administering (a) an amount of an inhibitor of vascular nitric oxide activity sufficient to decrease tumor blood flow or oxygenation, and (b) a hypoxic or acidotic chemotherapeutic agent.

In another aspect, the invention is directed to a method for treating a subject having a solid tumor comprising administering to the subject an amount of an inhibitor of vascular nitric oxide, such as a nitric oxide scavenger or a nitric oxide synthase inhibitor, in an amount sufficient to decrease tumor blood flow or tumor oxygenation, and administering hyperthermia therapy.

In another aspect, the invention is directed to a method for treating a subject having a solid tumor comprising administering to the subject an amount of a competitive inhibitor of nitric oxide synthase (e.g., a substrate analog) in an amount sufficient to decrease tumor blood flow or tumor oxygenation, and, subsequently, administering a substrate of nitric oxide synthase, in order to selectively decrease the reduction of blood flow and oxygenation in normal tissue. In a preferred aspect, the substrate is administered in an amount effective to restore normal blood flow and oxygenation to normal tissue.

In a further aspect, the present invention provides a pharmaceutical composition for treating solid tumors comprising a nitric oxide scavenger or a nitric oxide synthase inhibitor and a hypoxic cytotoxin or acidotic cytotoxin.

In a further aspect, the present invention provides a pharmaceutical composition for treating solid tumors comprising a substrate of nitric oxide synthase. The invention also provides a kit comprising in separate containers: an inhibitor of vascular nitric oxide synthase in a pharmaceutically acceptable form, and a substrate of nitric oxide synthase in a pharmaceutically acceptable form.

The present invention combines therapeutic modalities to selectively target various solid tumor populations that vary in their microenvironmental conditions. One advantage of the present invention is that the tumor-specific toxicity of hypoxic cytotoxins toward hypoxic tumors can be enhanced, thus increasing the efficiency of the hypoxic cytotoxin. Increased toxic efficiency can allow lower doses, and thus, reductions in toxic side effects, or more effective therapy leading to better outcomes. Another particular advantage of the present invention is that it permits therapy of aerobic cells using hypoxic cytotoxins. Furthermore, the invention allows for powerful combination therapies, for example radiation, which is effective against aerobic tumor cells, with hyperthermia and drugs that are effective against hypoxic and acidotic cells. This combination achieves a more uniform cell kill over all physiologic subtypes than any of the treatments alone.

Another advantage of the invention is that it allows applications of treatment regimens against subpopulations of tumor cells while having minimum effects on normal tissue.

The present invention is illustrated by way of example by the demonstration of the feasibility of the therapeutic approach of combining NO inhibition with the hypoxic cell cytotoxin mitomycin C. In a specific example, infra, a trend toward enhancement of tumor growth delay was observed when tumor-bearing animals were treated with stroma-free hemoglobin (a NO scavenger) 40 min after administration of mitomycin C, as compared with mitomycin C alone. In another specific example, infra, NO synthase inhibition by L-NMA reduced blood flow in tumor tissue while the effect of the inhibitor was selectively reversed in normal tissue by the administration of L-arginine.

4. DESCRIPTION OF THE FIGURES

FIG. 1. Effect of intravenous administration of L-NMA on mean arteriolar blood pressure (MAP) (open squares, open circles, and crossed-squares) and heart rate (open diamonds, open triangles and closed diamonds) in Fischer 344 rats. Data are from 3 experiments.

Figure 2:
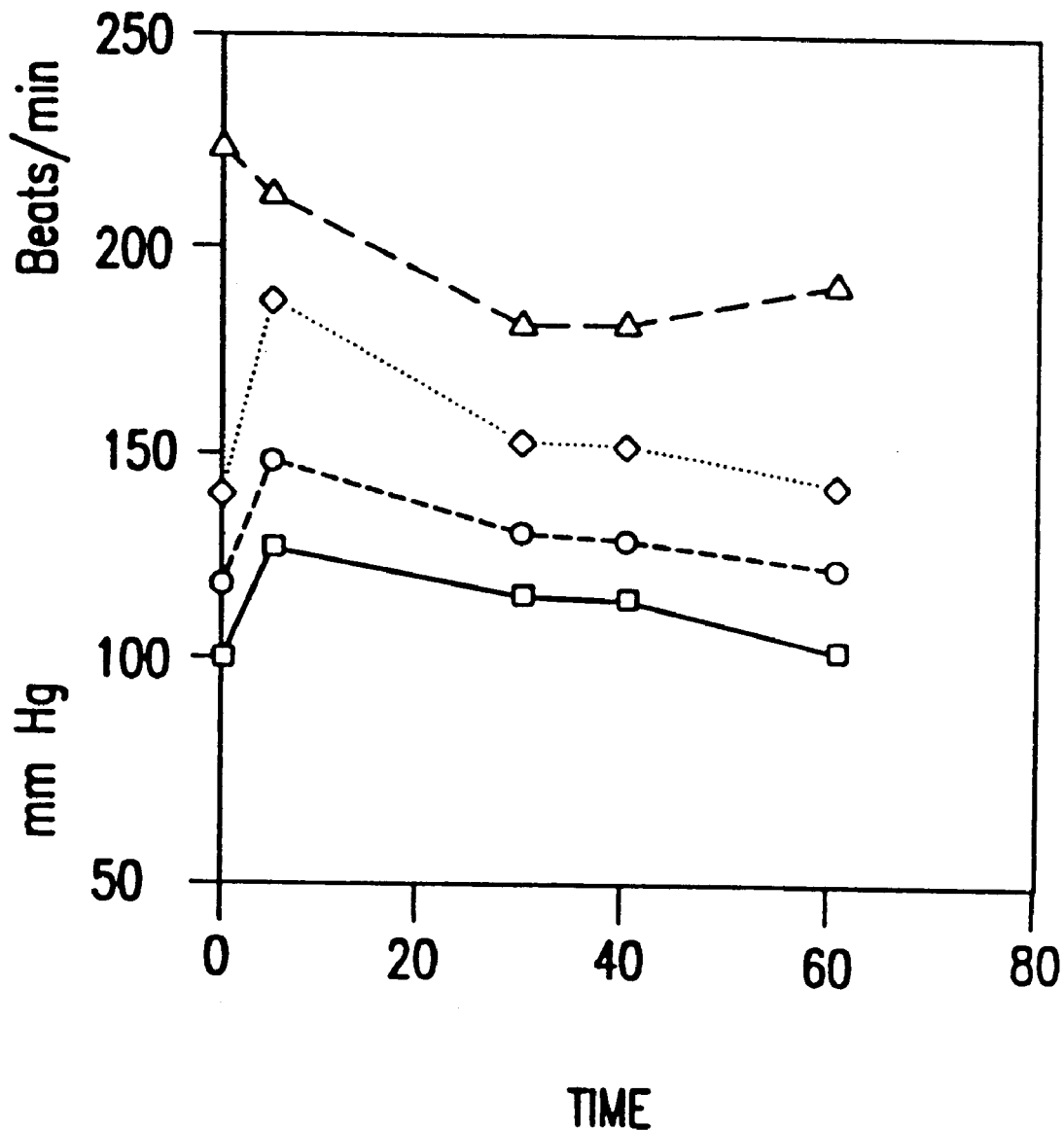

FIG. 2. Effect of intravenous cell free hemoglobin solution on arterial blood pressure and heart rate in Fischer 344 rats. Data were pooled from 5 experiments, and include measurements of diastolic blood pressure (open squares), systolic blood pressure (open diamonds) and mean blood pressure (open circles) in mm Hg, and heart rate (open triangles) in beats per minute.

Figure 3:
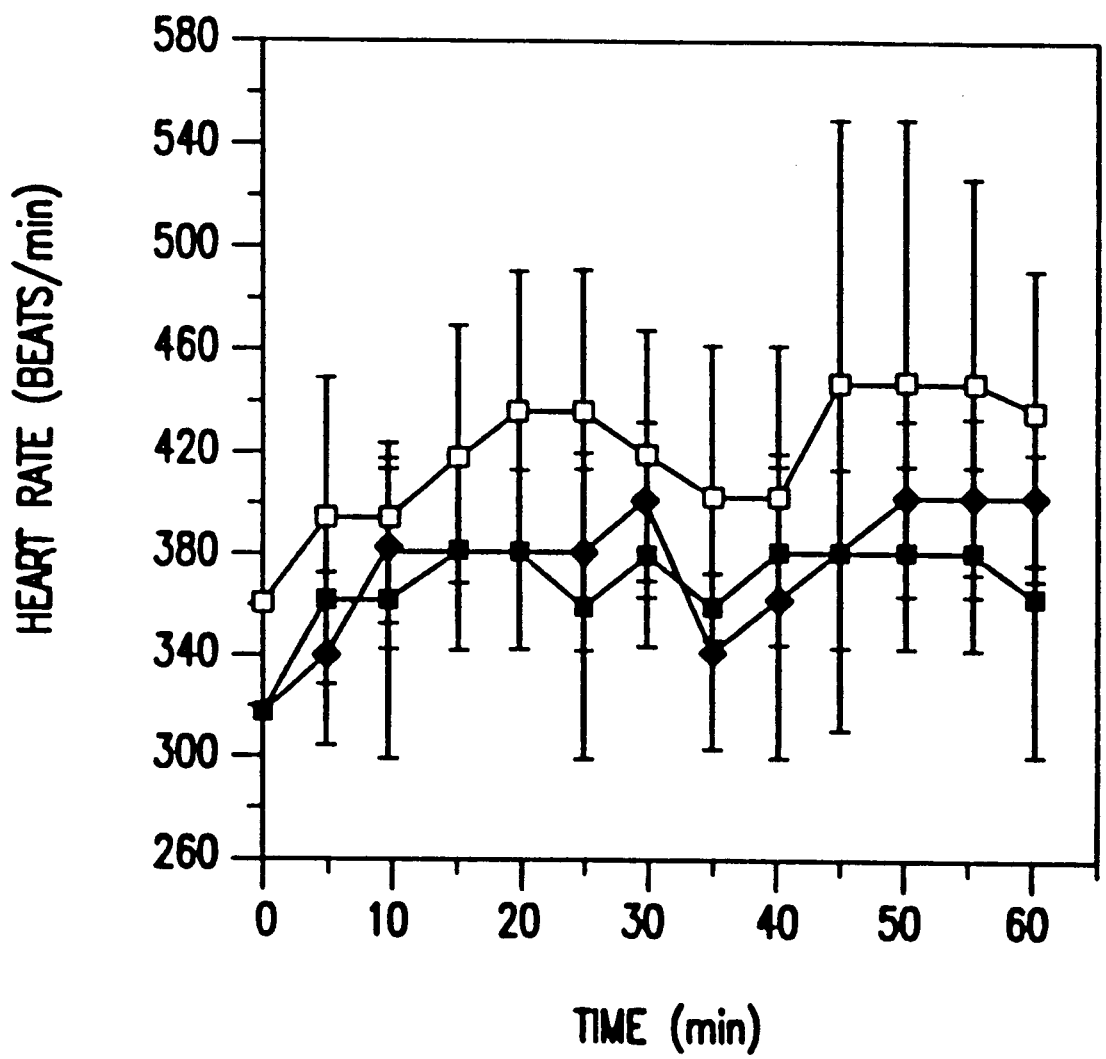

FIG. 3. Average heart rate (beats/min) over time of rats treated with albumin (open squares), hemoglobin $P_{50}9$ (solid diamonds) and hemoglobin $P_{50}32$ (solid squares). Data are averaged from three rats per experimental group.

Figure 4:
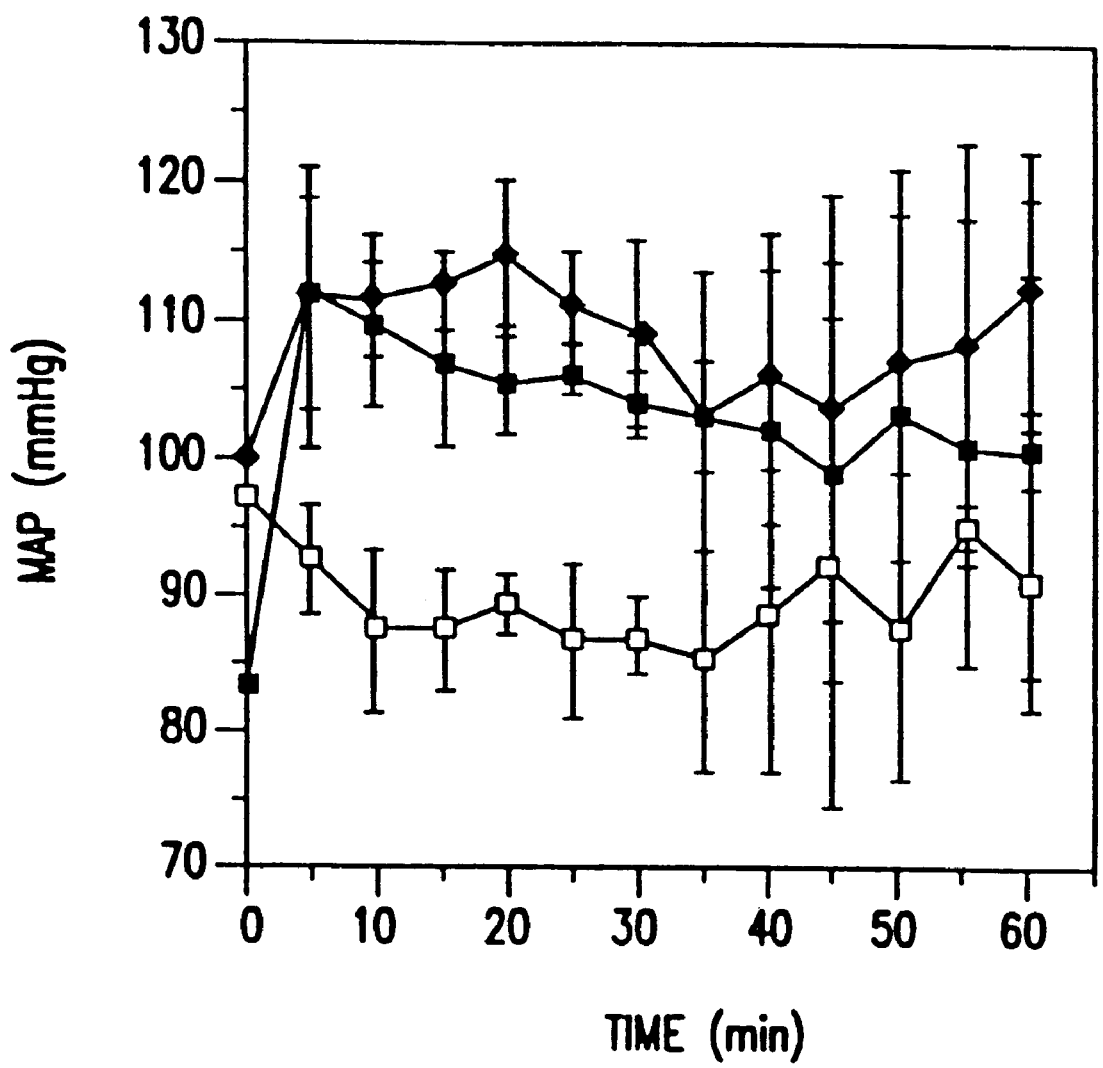

FIG. 4. Mean arteriolar pressure (MAP) in mm Hg over time for rats treated with albumin (open squares), hemoglobin p50 9 (solid diamonds) and hemoglobin p50 32 (solid squares). Data are averaged from three rats per experimental group.

Figure 5:
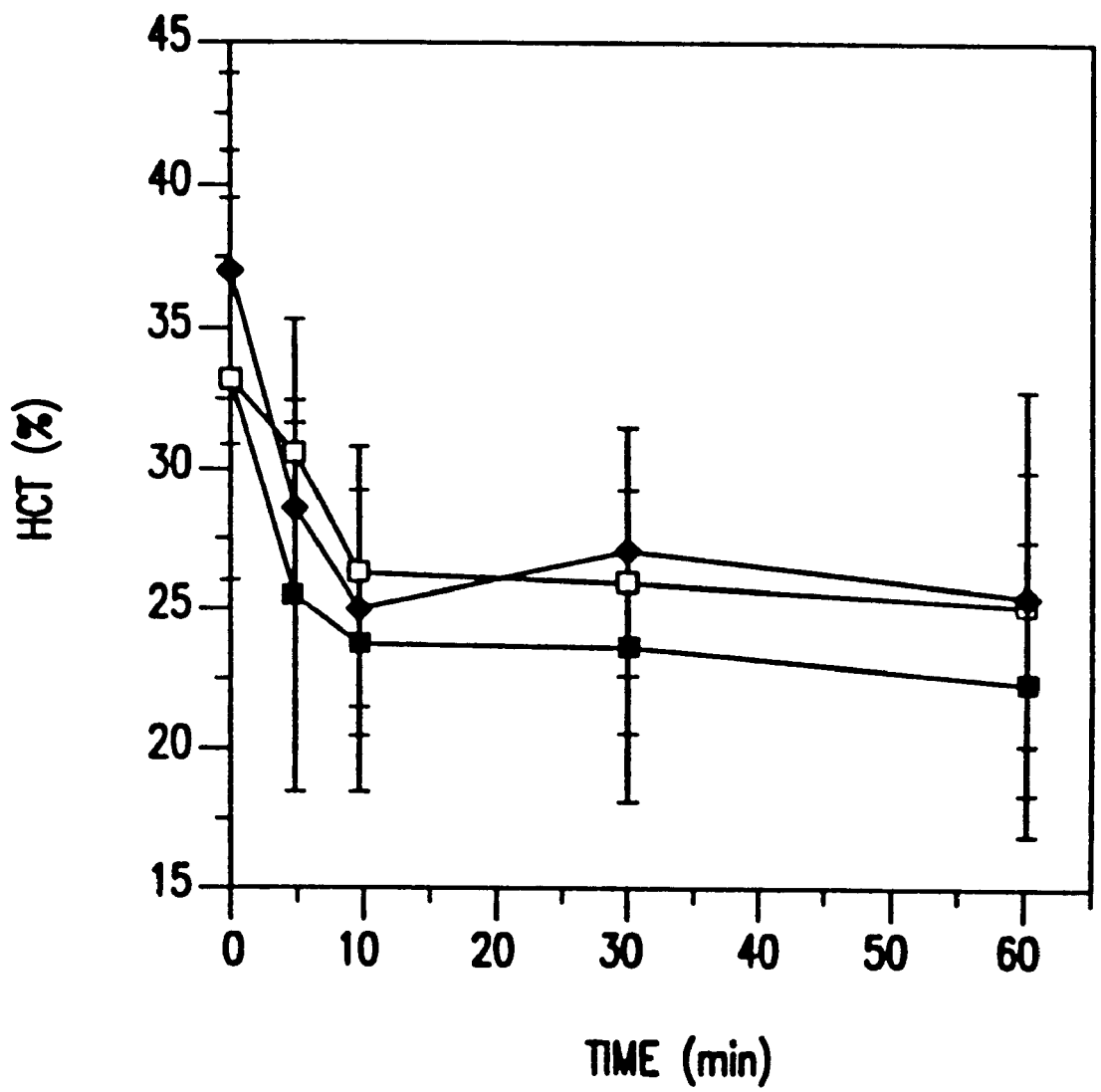

FIG. 5. Average hematocrit of rats treated with albumin (open squares), hemoglobin p50 9 (solid diamonds) and hemoglobin p50 32 (solid squares). Data are averaged from three rats per experimental group.

Figure 6:
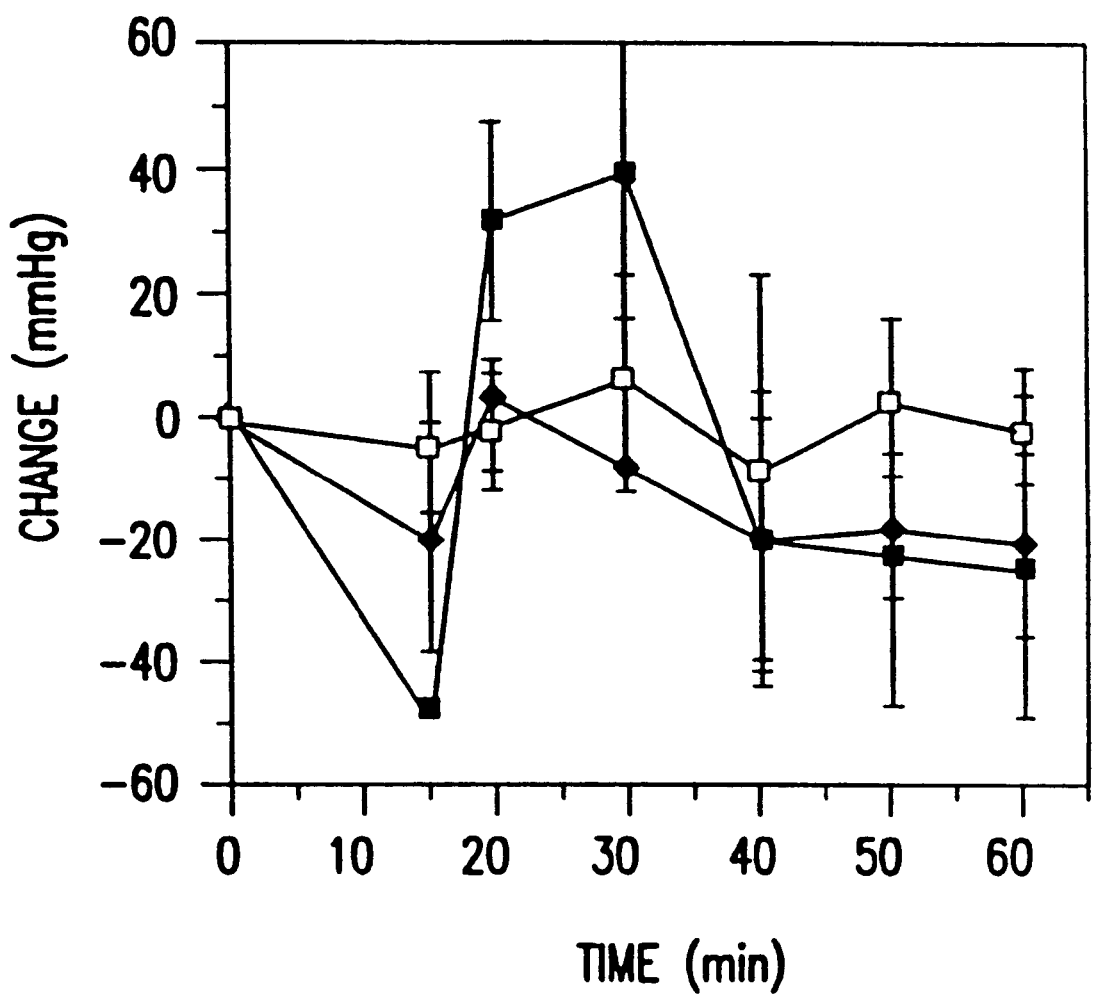

FIG. 6. Muscle oxygenation changes (mm Hg) in rats treated with albumin (open squares), hemoglobin p50 9 (solid diamonds) and hemoglobin p50 32 (solid squares). Data are averaged from three rats per experimental group.

Figure 7:
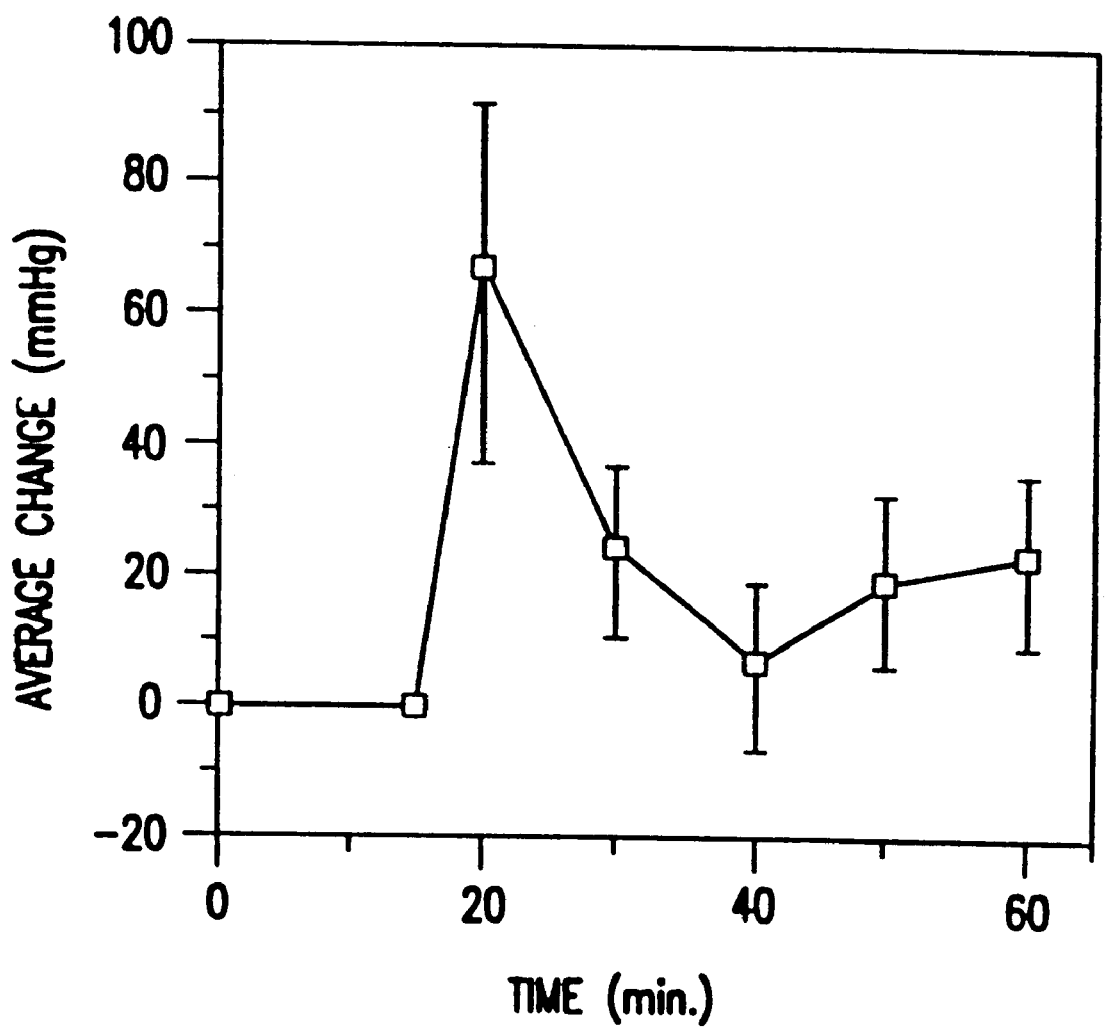

FIG. 7. Average tumor oxygenation changes (mm Hg) in three rats treated with albumin.

Figure 8:
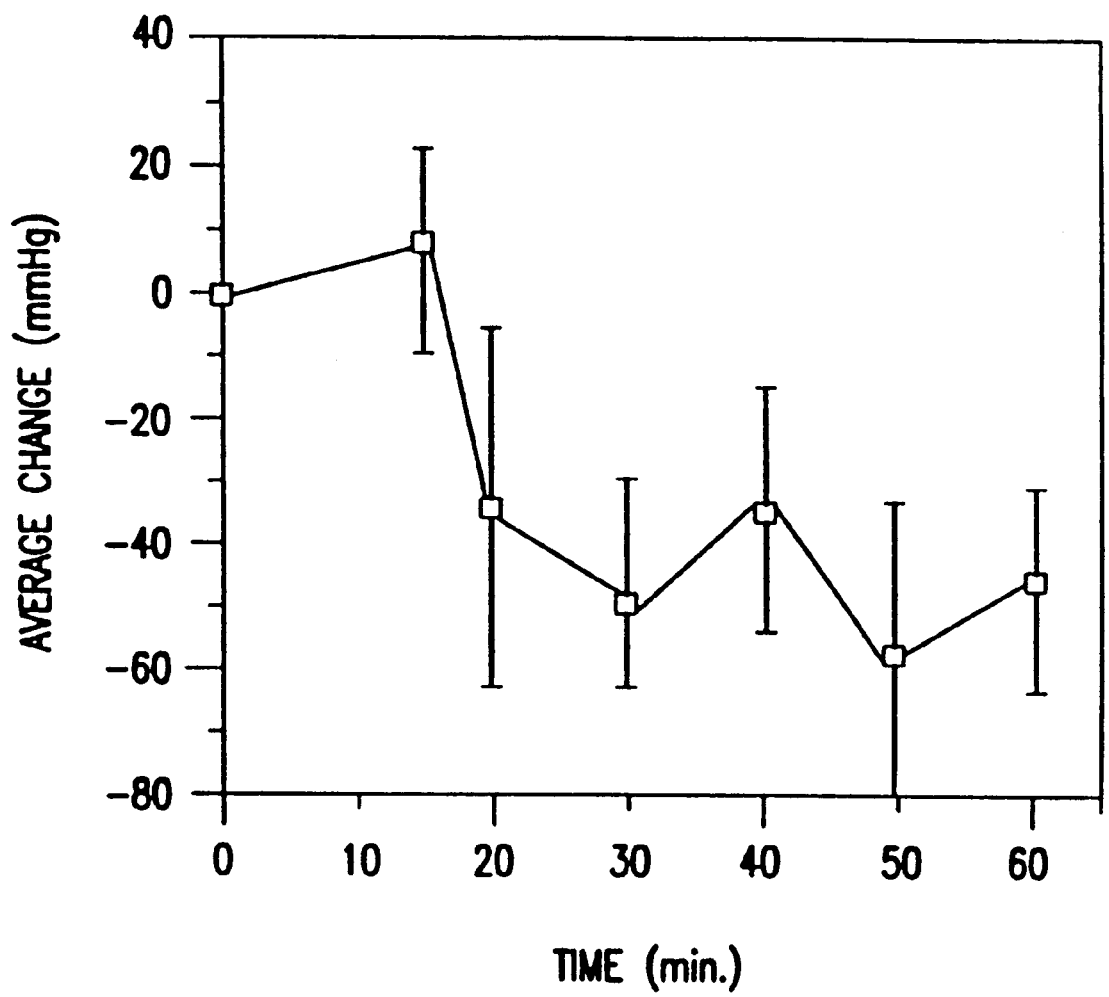

FIG. 8. Average tumor oxygenation changes (mm Hg) in three rats treated by hemoglobin p50 9.

Figure 9:
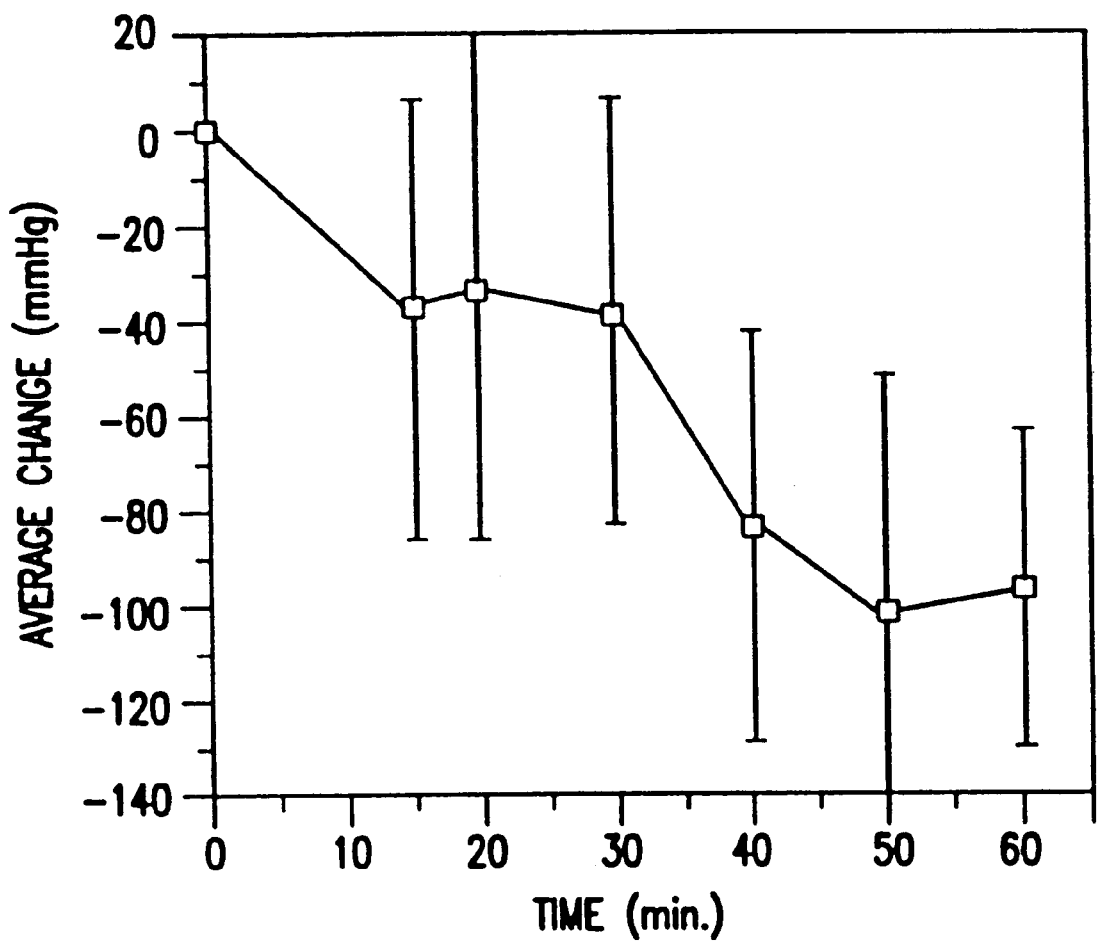

FIG. 9. Average tumor oxygenation changes (mm Hg) in three rats treated with hemoglobin p50 32.

Figure 10:
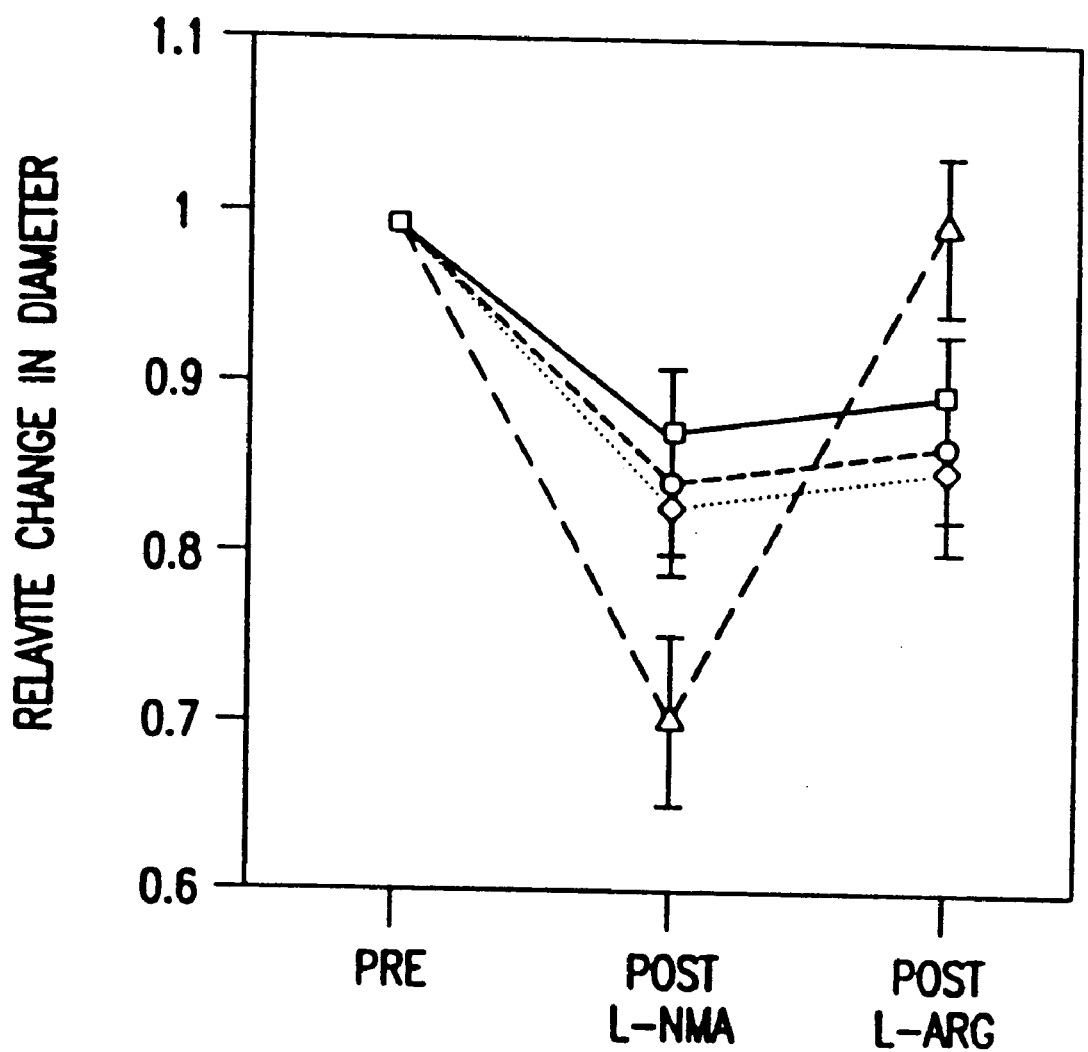

FIG. 10: Relative change in microvessel diameter after 60 min superfusion of L-NMA followed by 60 min superfusion of L-arginine. L-NMA significantly reduced diameters for all types of tumor preparation venules (tumor center, tumor periphery, normal near tumor) as well as for venules in control preparations (all p<0.05). Superfusion of L-arginine had negligible restoring effect on tumor preparation venules, but returned control venules to baseline diameter. Symbols represent mean±SEM. Open squares: tumor center; open diamond: tumor periphery; open circle: normal, near tumor; open triangle: control, no tumor.

Figure 11:
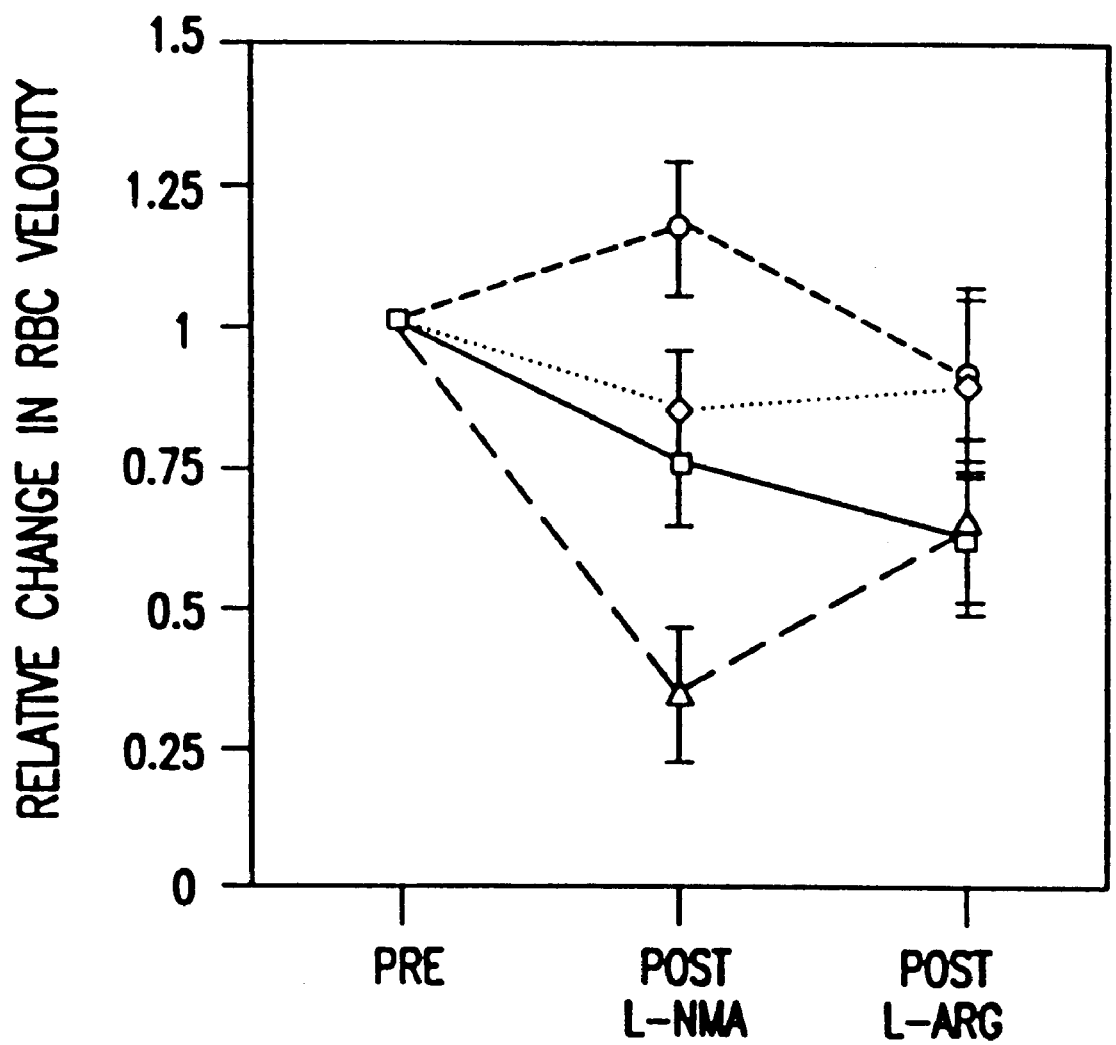

FIG. 11: Relative change in microvessel RBC velocity after 60 min superfusion of L-NMA followed by 60 min superfusion of L-arginine. L-NMA reduced RBC velocity of control and tumor center venules from baseline (both p<0.05). L-arginine returned RBC velocity to baseline levels in tumor periphery vessels, normal vessels near tumors, and control vessels, but RBC velocity in tumor center venules remained significantly reduced from baseline (p<0.05). Symbols represent mean±SEM. Open squares; tumor center; open diamond: tumor periphery; open circle: normal, near tumor; open triangle: control, no tumor.

Figure 12:
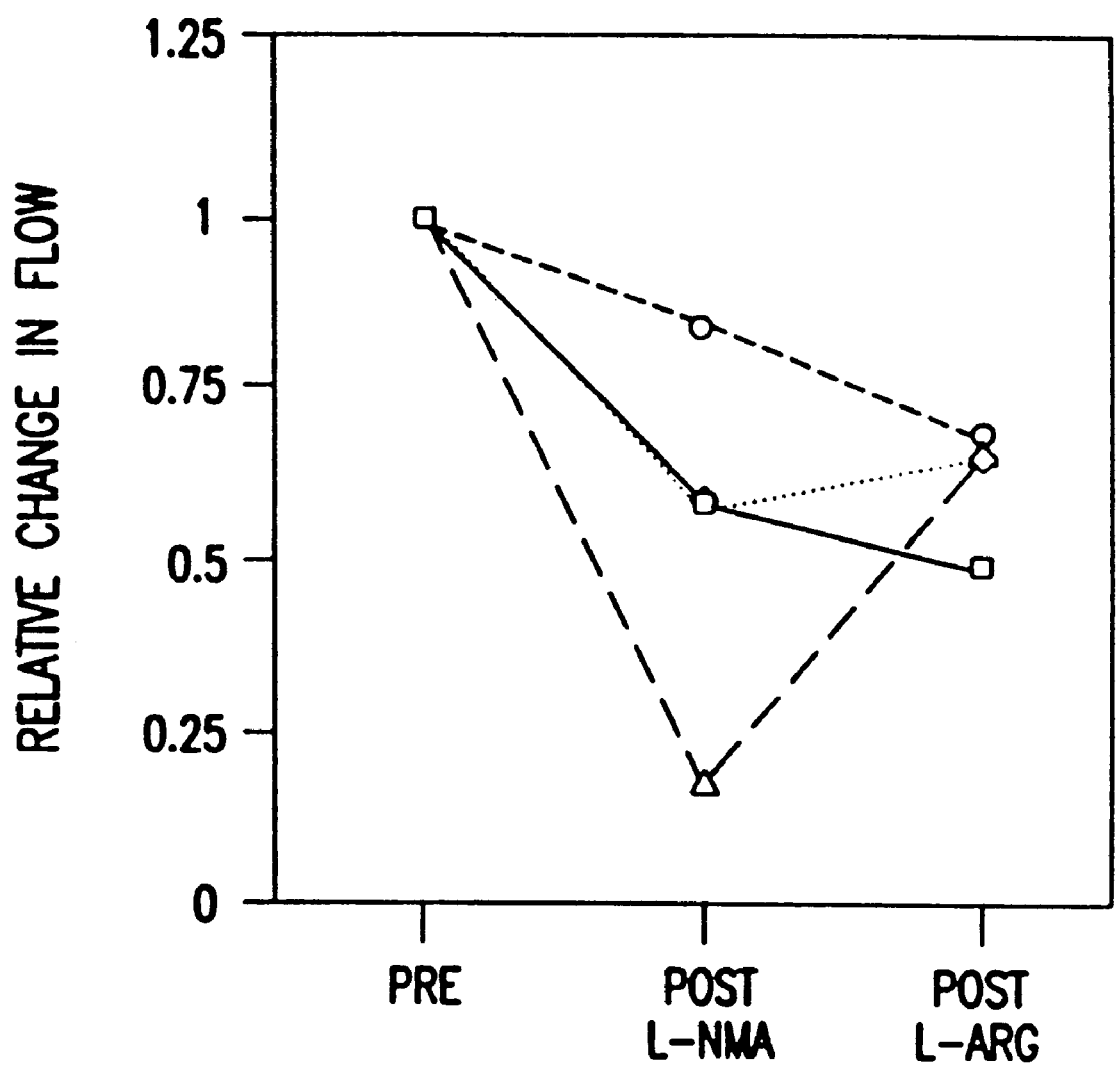

FIG. 12: Relative change in microvessel flow after 60 min superfusion of L-NMA followed by 60 min superfusion of L-arginine. L-NMA reduced relative flow 43% in tumor center and peripheral tumor vessels, and 83% in control vessels. L-arginine restored peripheral tumor flow to the same levels observed in normal vessels near tumors. Flow in central tumor vessels continued to decrease in the presence of L-arginine. The graph is provided to illustrate the interaction between diameter and RBC velocity. Open squares: tumor center; open diamond: tumor periphery; open circle: normal, near tumor; open triangle: control, no tumor.

Figure 13:
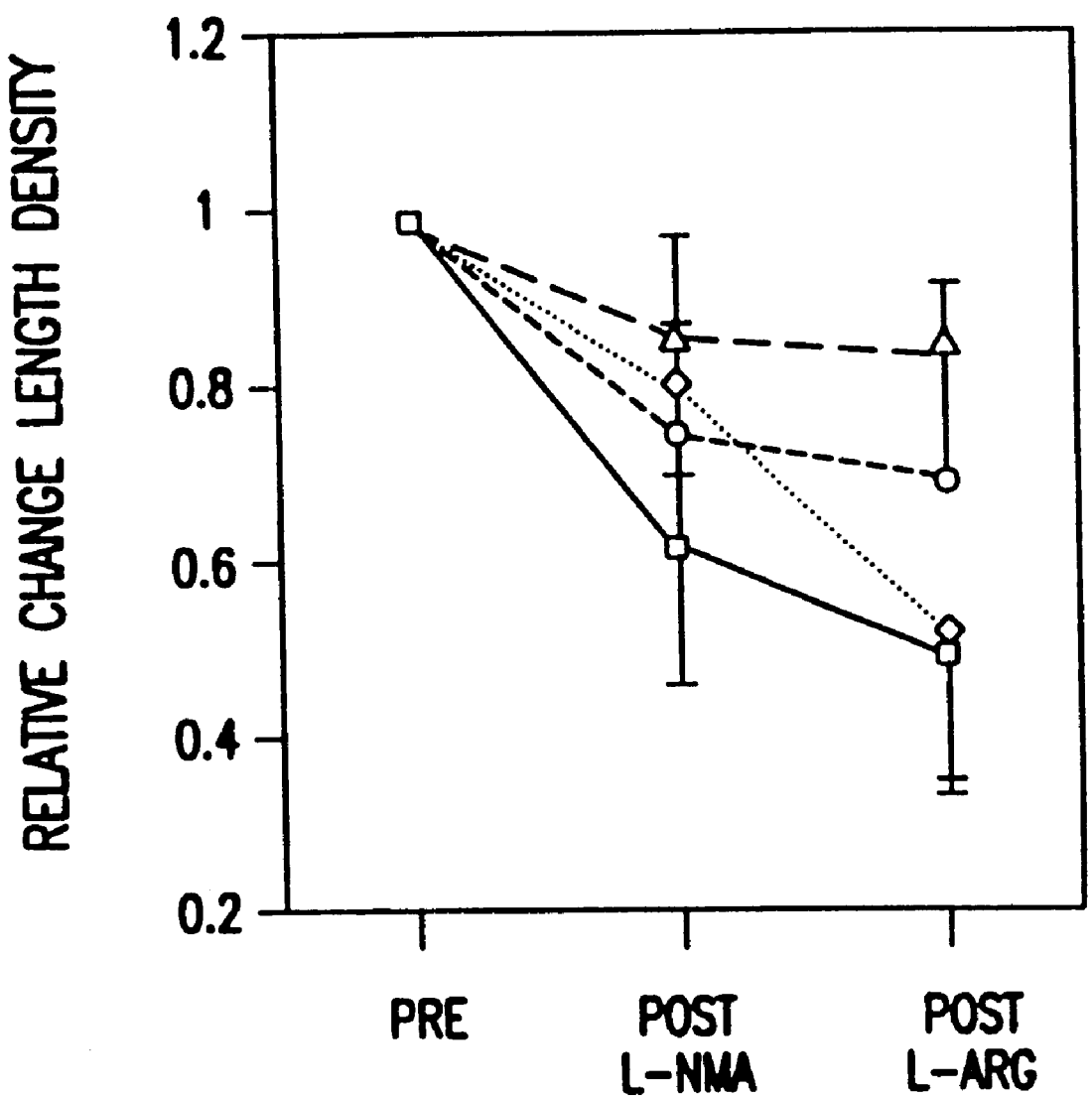

FIG. 13. Relative change in vessel length density after 60 min superfusion of L-NMA followed by 60 min superfusion of L-arginine. Although not statistically significant, L-NMA may reduce vessel length density in tumor vessels (p=0.07, tumor center; p=0.08 for both tumor periphery and normal vessels near tumors). Vessel length density further decreased following L-arginine for both tumor center and peripheral tumor vessels (p=0.01 and p=0.05, respectively). Symbols represent mean±SEM. Open squares: tumor center; open diamond: tumor periphery; open circle: normal, near tumor; open triangle: control, no tumor.

Figure 14:
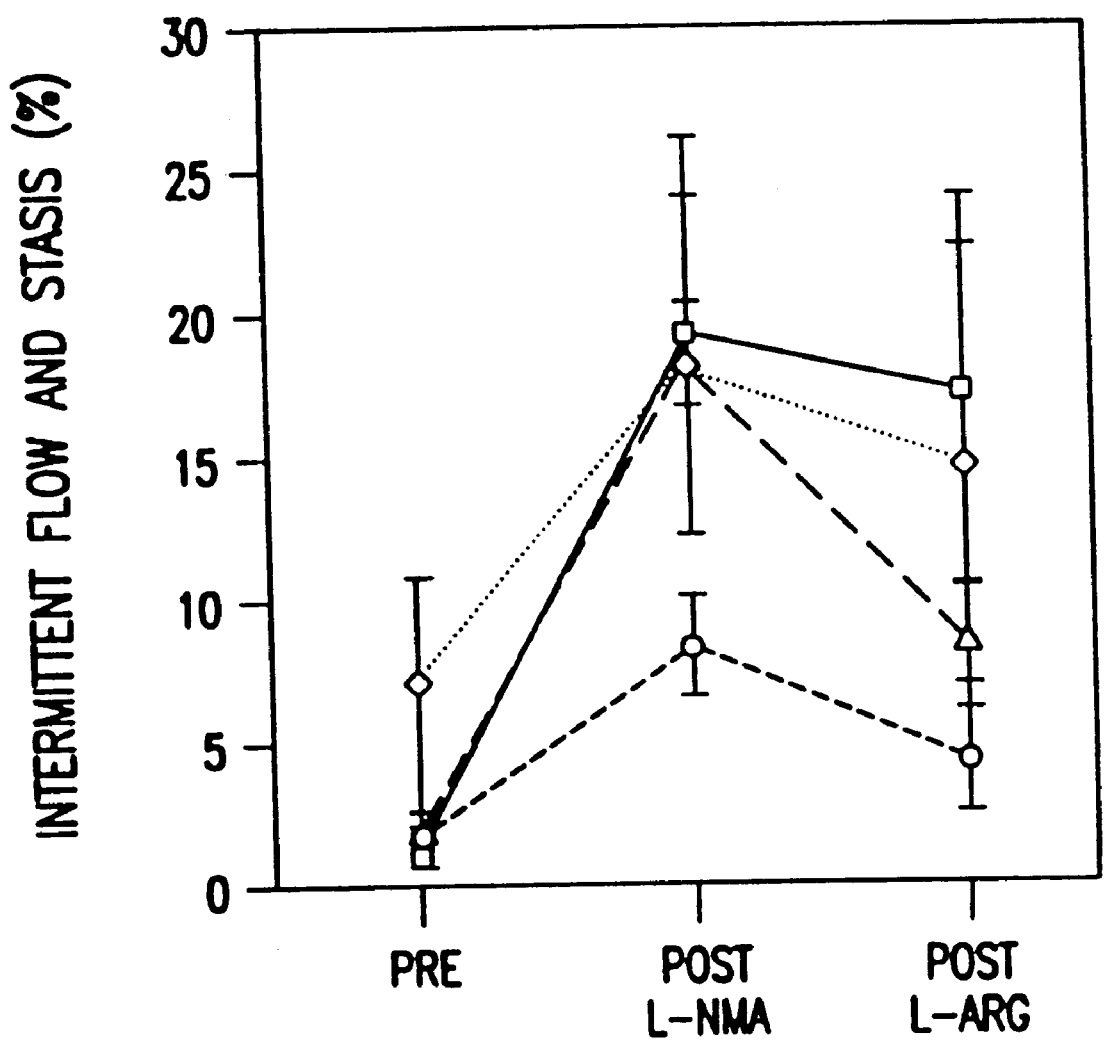

FIG. 14: Percent of vessels showing intermittent flow or stasis after 60 min superfusion of L-NMA followed by 60 min superfusion of L-arginine. L-NMA increased intermittent flow and stasis in central tumor vessels relative to baseline (p=0.03). Intermittent flow and stasis may increase with L-NMA in peripheral tumor vessels and normal vessels near tumors (p=0.06 for both). L-arginine returned intermittent flow and stasis to baseline levels for all vessel types. Symbols represent mean±SEM. Open squares: tumor center; open diamond: tumor periphery; open circle: normal, near tumor; open triangle: control, no tumor.

5. DETAILED DESCRIPTION OF THE INVENTION

The present invention is directed to the use of an inhibitor of nitric oxide (NO) activity, such as a NO scavenger or an NO synthase inhibitor, as an antitumor therapy to reduce tumor blood flow and oxygenation, or as an adjunct therapy in the treatment of solid tumors with (1) a chemotherapeutic agent, in particular a hypoxic cytotoxin or an acidotic cytotoxin, and/or with (2) hyperthermia.

According to the present invention, inhibition of NO, either with inhibitors of NO synthesis or NO scavengers, selectively reduces blood flow in solid tumors, and leads to irreversible vascular stasis in some tumor vessels. The effects of NO reduction in normal tissue are less frequent and much less extensive, indicating that reduction in NO concentration creates a selective effect in the tumor. Inhibitors of NO synthesis and NO scavengers cause minimal side effects, and these side effects consist primarily of a mild and transient pressor effect.

The present inventors have discovered that NO synthase inhibition can be used to effect preferential tumor blood flow reduction, since the tumor blood flow reduction is irreversible even upon administration of an NO synthase substrate, while blood flow reduction in normal tissue is reversed by administration of such a substrate. The present invention provides a method selectively to decrease blood flow reduction in normal tissue resulting from the administration of a nitric oxide synthase inhibitor (optionally, the inhibitor being administered concurrently or sequentially with the administration of a hypoxic or acidotic chemotherapeutic agent or with hyperthermia) by administering a substrate of NO synthase.

According to the invention, therapeutic administration of an NO scavenger or NO synthase inhibitor in conjunction with administration of a chemotherapeutic agent leads to enhanced anti-tumor chemotherapeutic effectiveness. Therapeutic administration of an NO scavenger or NO synthase inhibitor in conjunction with hyperthermia therapy leads to enhanced toxicity toward the solid tumor. The hypoxic cytotoxins are cytotoxins that are effectively cytotoxic to hypoxic or acidic cells or under hypoxic conditions. The acidotic cytotoxins are agents whose cytotoxicity is enhanced under acid pH conditions.

The present inventors have discovered that the physiological consequences of tumor blood flow reduction include reduction in the heat transfer capacity of a tumor, and the induction of hypoxia and acidosis. Hypoxia and acidosis contribute to hyperthermia cytotoxicity. Hyperthermia cytotoxicity is greatly enhanced in cells that demonstrate acute drops in pH, even when the magnitude of the drop is only a few tenths of pH.

According to the present invention, inhibition of NO, either with antagonists of NO synthase or scavenging of NO (e.g., with stroma free hemoglobin) reduces tumor blood flow and leads to tumor vascular stasis. The effect is achieved in tumor with only a mild and transient systemic pressor effect. Although not intending to be bound by any particular theory, it is believed that two mechanisms are responsible for this effect: (1) reduction in NO causes vasoconstriction in normal arterioles that feed the tumor, and (2) platelet aggregation is stimulated preferentially within tumor vessels, leading to microthrombus formation.

5.1. NO Scavengers

The present invention contemplates the use of any NO scavenger as an antitumor therapy to reduce tumor blood flow and oxygenation or as an adjunct therapy to potentiate or enhance the chemotherapeutic effect of a hypoxic or acidic cytotoxin, or to enhance the effect of hyperthermia therapy. As used herein, the term "NO scavenger" refers to any molecular entity that binds with free NO so as to reduce the concentration of NO locally or systemically. Such scavengers include, but are not limited to, metalloproteins, in particular heme containing proteins such as but not limited to hemoglobin, myoglobin, cytochrome-P-450, heme albumin, heme-containing peptides such as undecapeptide of cytochrome C, as well as water soluble hemoglobin analogs such as strapped heme (e.g., Traylor and Traylor, 1982, Ann. Rev. Biophys. Bioeng. 11:105–127) and picket fence porphyrin (Collman et al., 1975 J. Am. Chem. Soc. 97:1427–1439). In a preferred embodiment, the scavenger selected for use is one which, in vivo, in vitro, or animal model experiments, is shown to be capable of causing vascular stasis that is not reversed by L-arginine.

Use of many NO scavengers according to the present invention has the advantage of restricting NO reduction to the vasculature, without affecting intracellular NO production or extravascular NO activity. Thus, NO activity as a transduction mechanism for soluble guanylate cyclase in the nervous system and the function of immune cells, such as macrophages, will be minimally affected, thus reducing possible side effects of therapy with an NO scavenger. Macromolecular NO scavengers such as hemoglobin can become trapped in the perivascular space of a solid tumor, since the tumor vasculature is very leaky compared to normal tissue. Macromolecules such as hemoglobin do not readily pass into the perivascular space of normal tissue, so they are less likely to be trapped there. Trapping of an NO scavenger, such as hemoglobin, in the perivascular space of the tumor tends to restrict the NO scavenging effect to the tumor, thus enhancing tumor hypoxia with minimal effects on normal tissue.

In a preferred aspect of the invention, the NO scavenger is cell free hemoglobin (CFHb), also referred to as stroma free hemoglobin. Stroma-free hemoglobin may be obtained using procedures known in the art (see for example, PCT Application Publication No. WO 88/03408, published May 19, 1988; U.S. Pat. No. 4,001,401; Feola et al., 1983, Surgery Gynecology and Obstetrics 157:399–408; De Venuto et al., 1979, Surgery Gynecology and Obstetrics 149:417–436). For example, stroma-free hemoglobin may be obtained as follows: (a) obtaining whole blood; (b) separating red blood cells from other components of whole blood; (c) isolating the hemoglobin from the erythrocytes; and (d) separating the hemoglobin from stroma and other impurities.

Stroma-free hemoglobin can be prepared starting with erythrocytes in freshly drawn, outdated, or frozen packed cells or whole blood. The blood should be drawn in a sterile fashion into containers with sufficient anticoagulant activity to prevent clot formation.

In one embodiment, the erythrocytes are washed in a saline solution and centrifuged to separate red blood cells from white blood cells and to additionally remove free proteins (Feola et al., 1983, Surgery Gynecology and Obstetrics 157:399–408). In another embodiment, the red cells may be separated from other erythrocytes by passing through a semi-continuous type centrifuge as described in PCT Application Publication No. WO 88/03408, published May 19, 1988.

Hemoglobin may be isolated in one embodiment by diluting the red blood cell solution in water or an organic solvent at about 2 to about 10° C. to separate the hemoglobin in red blood cells from all cell debris (PCT Application Publication No. WO 88/03408, published May 19, 1988; U.S. Pat. No. 4,001,401; Feola et al., 1983, Surgery Gynecology and Obstetrics 157:399–408). In another embodiment, the hemoglobin is precipitated as a zinc complex by the addition of a zinc salt to a hemoglobin solution (De Venuto et al., 1979, Surgery Gynecology and Obstetrics. 149:417–436).

The isolated hemoglobin may in one embodiment be purified by ultrafiltration through for example a $0.5\mu$ pore filter which retains the cellular components and passes the hemoglobin.

Hemoglobin may also be obtained through other procedures known in the art. For example, bacterial strains (see for example Nagai and Hoffman, U.S. Pat. No. 5,028,588, issued Jul. 2, 1991) or yeast (see for example PCT Application Publication No. WO90/13645, published Nov. 15, 1990; U.S. patent application Ser. No. 07/876,290, filed Apr. 29, 1992, entitled "Expression of Recombinant Hemoglobin or Hemoglobin Variants in Yeast"), or other eukaryotic organisms may be engineered to produce hemoglobin by recombinant DNA techniques.

The hemoglobin may be, for example, any human hemoglobin or hemoglobin variant, including but not limited to HbA (alpha$_2$beta$_2$), HbA2 (alpha$_2$delta$_2$), HbF (alpha$_2$gamma$_2$), Hb Barts (gamma$_4$), HbH (beta$_4$), and Hb Portland I (zeta$_2$gamma$_2$), Hb Portland II (zeta$_2$beta$_2$), Hb Portland III (zeta$_2$delta$_2$), Hb Gower I (zeta$_2$epsilon$_2$), and Hb Gower II (alpha$_2$epsilon$_2$); as well as any other animal hemoglobin, e.g., bovine or porcine hemoglobin. Hemoglobin dimers are also useful, but unmodified hemoglobin monomers or dimers can lead to unacceptable renal toxicity.

The hemoglobin used in the method of the present invention may be chemically modified using procedures known in the art to form polymers of Hb tetramers (to increase half-life in circulation, e.g., Hb Porto Alegre), or to increase tetramer stability (to decrease renal toxicity) and/or lower oxygen affinity. Examples of chemical modifications to increase the tetramer stability include but are not limited to crosslinking with polyalkylene glycol (Iwashita, U.S. Pat. Nos. 4,412,989 and 4,301,144), with polyalkylene oxide (Iwasake, U.S. Pat. No. 4,670,417); with a polysaccharide (Nicolau, U.S. Pat. Nos. 4,321,259 and 4,473,563); with inositol phosphate (Wong, U.S. Pat. Nos. 4,710,488 and 4,650,786); with a bifunctional crosslinking agent (Morris et al., U.S. Pat. No. 4,061,736); with.insulin (Ajisaka, U.S. Pat. No. 4,377,512); and with a crosslinking agent so that the hemoglobin composition is intramolecularly crosslinked between lys 99 alpha$_1$, and lys 99 alpha$_2$ (Walder, U.S. Pat.

No. 4,598,064). Examples of chemical modifications to decrease the oxygen affinity of isolated hemoglobin include but are not limited to polymerization with pyridoxal phosphate (Sehgal et al., 1984, Surgery 95:433–438) and using reagents that mimic 2,3-diphosphoglycerate (DPG) (Bucci et al., U.S. Pat. No. 4,584,130).

In a further embodiment, the hemoglobin used in the method of the present invention may be a hemoglobin variant, a hemoglobin comprising a globin chain whose nucleotide sequence has been altered in such a fashion so as to result in the alteration of the structure or function of the hemoglobin, but so that the hemoglobin still remains functionally active as defined by the ability to reversibly bind to nitric oxide. Categories of hemoglobin variants include but are not limited to variants which autopolymerize; variants in which the tetramer does not dissociate under physiological conditions in vivo (e.g., Hb Rainier, beta-145 tyrosine is replaced by cysteine); variants with lowered intrinsic oxygen affinity, i.e., a hemoglobin having a p50 (p50 is the partial pressure of oxygen which results in 50% saturation of oxygen binding in hemoglobin) of at least about 10 mm Hg under physiological conditions (e.g., Hb Chico, beta-66 lysine is replaced by threonine; Hb Raleigh, beta-1 valine is replaced by alanine; Hb Titusville, alpha-94 aspartate is replaced by asparagine; Hb Beth Israel, beta-102 asparagine is replaced by serine; and Hb Kansas, beta-102 asparagine is replaced by threonine); variants that are stable in alkali (e.g., Motown/Hacettepe beta-127 or glutamine is replaced by glutamic acid); variants that are stable in acid; variants which have a lowered binding affinity to haptoglobin; variants with an increased intrinsic oxygen affinity, i.e., a hemoglobin having a P50 of at most about 1 mm Hg under physiological conditions (e.g., HbA Deer Lodge, beta-2 histidine is replaced by arginine, Labossiere et al., 1972, Clin. Biochem. 5:46–50; HbA Abruzzo, beta-143 histidine is replaced by arginine, Tentori et al., 1972, Clin. Chim. Acta 38:258–262; and HbA McKees Rocks, the coding sequence is altered so that the sequence encoding beta-145 tyrosine is replaced by a termination codon (Winslow et al., 1976, J. Clin. Invest. 57:772–781).

Acid stable hemoglobin variants may include those that replace the histidine at the alpha-103 position with an amino acid that is not ionized in acid (Perutz, 1974, Nature 247:341). Examples of such amino acids include serine, threonine, leucine, and alanine.

Haptoglobin nonbinding variants are those with variation in the alpha-Hb sequence in the region of amino acid numbers 121–127. This sequence has been shown to be involved in the binding of haptoglobin (McCormick and Atorssi, 1990, J. Prot. Chem. 9:735).

The globin variants may be produced by various methods known in the art. The manipulations which result in their production can occur at the gene or protein level. The globin may be altered at the gene level by site-specific mutagenesis using procedures known in the art. One approach which may be taken involves the use of synthetic oligonucleotides to construct variant globins with base substitutions. In one embodiment, a short oligonucleotide containing the mutation is synthesized and annealed to the single-stranded form of the wild-type globin gene (Zoller and Smith, 1984, DNA 3:479–488). The resulting short heteroduplex can serve as primer for second strand synthesis by DNA polymerase. At the 5' end, a single stranded nick is formed which is closed by DNA ligase. In another embodiment, two complementary oligonucleotides are synthesized, each containing the mutant sequence. The duplex that forms after annealing these complementary oligonucleotides can be joined to a larger DNA molecule by DNA ligase provided that the ends of both molecules have complementary single-stranded "sticky" ends. Another approach which may be taken involves introducing a small single-stranded gap in the DNA molecule followed by mis-repair DNA synthesis, i.e., the misincorporation of a non-complementary nucleotide in the gap (Botstein and Shortle, 1985, Science 229:1193). The incorporation of a thiol nucleotide into the gap may minimize the excision of the non-complementary nucleotide. Alternatively, a globin variant may be prepared by chemically synthesizing the DNA encoding the globin variant using procedures known in the art (see for example Froehler, 1986, Nucl. Acids Res. 14:5399–5407 and Caruthers et al., 1982, Genetic Engineering, J. K. Setlow and A. Hollaender eds., Plenum Press, New York, vol. 4, pp. 1–17). In a preferred embodiment, fragments of the variant globin are chemically synthesized and these fragments are subsequently ligated together. The resulting variant globin strands may be amplified using procedures known in the art, e.g., PCR technology, and subsequently inserted into a cloning vector as described supra. In a specific embodiment, site-specific mutants may be created by introducing mismatches into the oligonucleotides used to prime the PCR amplification (Jones and Howard, 1990, Biotechniques 8:178–180).

Manipulations of the globin sequence may be carried out at the protein level. Any of numerous chemical modifications may be carried out by known techniques including but not limited to specific chemical cleavage by cyanogen bromide, trypsin, chymotrypsin, papain, V8 protease, NaBH$_4$; acetylation, formylation, oxidation, reduction; etc. Alternatively, the variant globin protein may be chemically synthesized using procedures known in the art, such as commercially available peptide synthesizers and the like. Such standard techniques of polypeptide synthesis can be found described in such publications as Merrifield, 1963, J. Chem. Soc. 85:2149–2154 and Hunkapillar et al., 1984, Nature (London) 310:105–111.

Any of the foregoing variants can be tested for NO scavenging activity, e.g., according to the assay described in Sections 6 and 7, infra.

The hemoglobin that is used is preferably of mammalian origin, and can be from pigs, cows, dogs, cats, mice, rats, horses, primates such as monkeys and chimpanzees, and is most preferably human. In a specific embodiment, infra, the NO scavenger that is used is cell free hemoglobin of bovine origin.

5.2. Inhibitors of NO Synthesis

The present invention contemplates the use of any inhibitor of NO synthase as an antitumor therapy to reduce tumor blood flow and oxygenation or as an adjunct therapy to potentiate or enhance the chemotherapeutic effect of a hypoxic or acidic cytotoxin, or to enhance the effect of hyperthermia therapy. As used herein, the term "NO synthase inhibitor" refers to any competitive or non-competitive inhibitor of NO synthase.

In a preferred aspect of the invention, the NO synthase inhibitor is an arginine analog, such as aminoguanidine or methyl guanidine, and $N^G$-substituted arginine or an $N^G,N^G$-disubstituted arginine. Preferably, the substituted arginine is of the L configuration. Examples of substituted L-arginines for use as NO synthase inhibitors according to the invention include, but are not limited to, $N^G$-amino-L-arginine, $N^G$-nitro-L-arginine, $N^G$-alkyl-L-arginines such as $N^G$-methyl-L-arginine or $N^G$-monomethyl-L-arginine (often abbreviated NMMA, L-NMA or L-NMMA), $N^G$-ethyl-L- arginine, $N^G$-propyl-L-arginine, or $N^G$-butyl-L-arginine, $N^G$-nitro-L-arginine methyl ester (often abbreviated NAME or L-NAME), and N-iminoethyl-L-ornithine (often abbreviated NIO or L-NIO). These inhibitors are available from commercial sources, e.g., Calbiochem, Sigma, and Aldrich.

In another embodiment, an inhibitor of the NO synthase cofactor tetrahydropterin can be used. One such inhibitor is aminopterin.

In a specific example, infra, the NO synthase inhibitor that is used is $N^G$-monomethyl-L-arginine, abbreviated L-NMA).

5.2.1. Other Inhibitors of NO Activity

In addition to inhibitors of NO synthase, the present invention contemplates use of inhibitors of the second messenger system activated by NO, particularly the second messengers (downstream signal mediators) guanylate cyclase and cyclic GMP. A non-limiting example of guanylate cyclase inhibition is methylene blue. Cyclic GMP activity can be inhibited by aminoguanidine, such as M&B 22948.

5.2.2. Reversal of NO Synthesis Inhibition in Normal Tissue

The present invention also contemplates the therapeutic administration of an NO synthase inhibitor (a competitive inhibitor, e.g., a substrate analog) followed by administration of an NO synthase substrate so as to selectively reverse any effect of the inhibitor on normal tissue. As shown by way of example infra, the effect of the inhibitor on the tumor tissue is irreversible.

NO synthase substrates which can be used include but are not limited to guanidino succinate and L-arginine. In a specific embodiment, the NO synthase substrate that is used is L-arginine.

5.3. Therapeutic Methods and Compositions

The present invention is directed to methods for treating a subject having a solid tumor comprising administering an inhibitor of NO activity as an antitumor therapy to reduce tumor blood flow and oxygenation or as an adjunct therapy to potentiate or enhance the chemotherapeutic effect of a hypoxic or acidic cytotoxin, or to enhance the effect of hyperthermia therapy. The invention is also directed to the administration of a NO synthase inhibitor (a competitive inhibitor, e.g., a substrate analog) followed by the administration of a NO synthase substrate so as to alleviate any effects of the inhibitor on normal tissue. Preferably the subject is an animal, more preferably a mammal, and most preferably a human. However, the present invention is also directed to treatment of tumors of domestic animals, such as feline or canine subject, and farm animals, such as but not limited to bovine, equine and porcine subjects. In a specific embodiment, infra, the therapeutic method of the invention is effective to inhibit growth of a human tumor xenograft in a mouse.

Preferably the therapeutic methods of the invention result in an increase in tumor regression rate (response rate), local tumor control and/or reduction in the frequency of or elimination of growth of metastases. The therapeutic approach is directed to tumors that are large enough to be vascularized. Enhanced local control of a vascularized tumor reduces the probability of metastases by causing irreversible vascular stasis and by enhanced tumor cell kill. The therapeutic approach could be used for small metastases as well, in conjunction with systemic chemotherapy of the types discussed above.

According to the present invention, the NO scavenger, as described in Section 5.1, supra, or the NO synthase inhibitor, or the NO synthase substrate can be administered parenterally, i.e., via an intraperitoneal, intravenous, perioral, subcutaneous, intramuscular, intraarterial, etc. The preferred route of parenteral administration is intravenous. Preferably the NO scavenger or the NO synthase inhibitor or the NO synthase substrate is prepared in an admixture with a pharmaceutically acceptable carrier. The term "carrier" refers to diluents, excipients and the like for use in preparing admixtures of a pharmaceutical composition. Pharmaceutically acceptable carriers include but are not limited to sterile water, saline, buffered saline, dextrose solution, preferably such physiologically compatible buffers as Hank's or Ringer's solution, physiological saline, a mixture consisting of saline and glucose, and heparinized sodium-citrate-citric acid-dextrose solution and the like. As used herein, the term "pharmaceutically acceptable" means approved by a regulatory agency of the Federal or a state government or listed in the U.S. Pharmacopeia or other generally recognized pharmacopeia for use in animals, and more particularly in humans.

Techniques and formulations for administering the compositions may be found in *Remington's Pharmaceutical Sciences,* Meade Publishing Col., Easton, Pa., latest edition.

Generally, the NO scavenger or NO synthase inhibitor or NO synthase substrate is administered in a single bolus dose whether administered alone or in connection with chemotherapy or hyperthermia therapy, although the present invention also contemplates sustained administration, e.g., via an IV drip or pump, or administration in multiple boluses.

In a specific aspect, the invention also provides kits comprising in a container the NO scavenger or NO synthase inhibitor or NO synthase substrate in pharmaceutically acceptable form; e.g., lyophilized or in admixture with a pharmaceutically acceptable carrier. In one embodiment, a kit comprises in separate containers effective amounts of an NO synthase inhibitor and an NO synthase substrate.

5.3.1. Administration of Inhibitors of NO Activity

The present invention contemplates administration of an inhibitor of NO activity, such as a nitric oxide scavenger or an NO synthase inhibitor, as an antitumor therapy to reduce tumor blood flow and oxygenation.

Preferably the therapeutic methods of the invention result in an increase in tumor regression rate (response rate), local tumor control and/or reduction in the frequency of or elimination of growth of metastases. The therapeutic approach is directed to tumors that are large enough to be vascularized. Enhanced local control of a vascularized tumor reduces the probability of metastases by causing irreversible vascular stasis, and by enhanced tumor cell kill.

The dose of the NO scavenger or NO synthase inhibitor to be administered is a dose effective to reduce blood flow or the level of oxygenation in a tumor, e.g., as detected by such ability in vivo, or as extrapolated from in vitro assays or from the animal model systems as described in Sections 6 and 7, infra. For example, if the NO scavenger is cell free hemoglobin, in one embodiment, the dose (in g of scavenger per mass of the subject in kg) can be from about 0.01 g/kg to about 10 g/kg; in a specific example, infra, the dose is about 0.1 g/kg, which represents less than 5% of the total blood volume of the animal. If the NO synthase inhibitor is a substituted arginine, in a specific embodiment, the dose can be from about 0.1 mg/kg to about 100 mg/kg. In a specific embodiment, infra, the synthase inhibitor is L-NMA administered at a dose of 3.0 mg/kg.

The present invention also contemplates the administration of an NO synthase inhibitor, followed by the administration of a NO synthase substrate, so as to effect the selective reduction of tumor blood flow and increased tumor hypoxic cell fraction, while tending to restore normal tissue blood flow. Preferably, the NO synthase substrate is administered from 10 minutes to 4 hours after the administration of the NO synthase inhibitor.

5.3.2. Administration with Hypoxic and Acidic Cytotoxins

The present invention contemplates administration of an NO scavenger or an NO synthase inhibitor in conjunction with a hypoxic or acidic chemotherapeutic agent of the invention. Hypoxic cytotoxins include, but are not limited to mitomycin C, analogs of mitomycin C, and drugs of the nitroimidazole class, such as etanidazole. The chemotherapeutic agents can also be agents whose cytotoxicity is enhanced under acid pH conditions, particularly during hyperthermia. Acidotic cytotoxins include, but are not limited to, cisplatin, analogs of cisplatin, bleomycin, flavone acetic acid and etanidazole.

According to the present invention, the NO scavenger or NO synthase inhibitor should be administered so that vascular stasis occurs after the hypoxic cytotoxin or acidotic cytotoxin has completely infused within the tumor. In one embodiment, the NO scavenger or NO synthase inhibitor can be administered simultaneously with administration of the chemotherapeutic agent. Alternatively, the agents can be administered sequentially, preferably with the chemotherapeutic agent administered first, followed by the NO scavenger or the NO synthase inhibitor. Generally, if administered sequentially, the NO scavenger or NO synthase inhibitor is administered about 15 minutes to about 60 minutes after the chemotherapeutic agent. However, if the NO scavenger or NO synthase inhibitor is very slow acting, its administration can precede administration of the cytotoxin.

The present invention also contemplates the administration of an NO synthase inhibitor, either simultaneously or sequentially with a hypoxic or acidotic chemotherapeutic agent, followed by the administration of a NO synthase substrate (e.g., L-arginine), so as to effect the selective reduction of tumor blood flow and increased tumor hypoxic cell fraction, while tending to restore normal tissue blood flow. Preferably, the NO synthase substrate is administered from 10 minutes to 4 hours after the administration of the NO synthase inhibitor.

Generally, the dose of the chemotherapeutic agent will be a dose found to be effective for chemotherapy. For the therapy of a hypoxic tumor, the dose of the chemotherapeutic agent may be less than the standard amount administered for chemotherapy.

The dose of the NO scavenger or NO synthase inhibitor to be administered is a dose effective to reduce blood flow or the level of oxygenation in a tumor, e.g., as detected by such ability in vivo, in in vitro assays, or in the animal model systems as described in Sections 6 and 7, infra. For example, if the NO scavenger is cell free hemoglobin, the dose (in g of scavenger per mass of the subject in kg) can be from about 0.01 g/kg to about 10 g/kg; in a specific example, infra, the dose is about 0.1 g/kg, which represents less that 5% of the total blood volume of the animal. If the NO synthase inhibitor is a substituted arginine, the dose can be from about 0.1 mg/kg to about 100 mg/kg. In a specific embodiment, infra, the synthase inhibitor is L-NMA administered at a dose of 3.0 mg/kg. In an embodiment in which an NO synthase substrate is administered, the dose of the NO synthase substrate is preferably from 30 mg/kg to 300 mg/kg.

In a specific aspect of the invention, the NO scavenger, preferably cell free hemoglobin, or the NO synthase inhibitor, and a hypoxic or acidic cytotoxin can be prepared in a pharmaceutical composition with a pharmaceutically acceptable carrier.

5.3.3. Administration with Hyperthermia

In another aspect, the present invention contemplates administration of an NO scavenger or an NO synthase inhibitor in conjunction with hyperthermia therapy for the treatment of a solid tumor. Hyperthermia therapy refers to use of physical agents, such as but not limited to microwaves, ultrasound, or other heating element for local or regional heating, or radiant heat for total body hyperthermia. Generally, tumor vasculature cannot respond to heat stress as well as normal tissue, and reducing tumor blood flow enhances this effect. Administration of an NO scavenger or an NO synthase inhibitor further reduces the ability of tumors to responds to heat stress. Furthermore, the present methods can help overcome some of the limitations of hyperthermia therapy that result from the non-uniformity of the temperature within the tumor, particularly regions of the tumor with relatively high blood flow.

Moreover, by reducing tumor blood flow, metabolism in the tumor becomes more anaerobic, resulting in production of lactic acid and a decrease in pH. Decreasing pH in a tumor significantly increases the effectiveness of hyperthermia therapy, e.g., by as much as five orders of magnitude.

According to the present invention, inhibition of NO activity precedes hyperthermia therapy so that tumor hypoxia and acidosis of the tumor can occur or increase by the time of hyperthermia application. Thus, in a specific aspect of the invention, the NO scavenger or the NO synthase inhibitor is administered about 10 min to 12 hours prior to hyperthermia therapy; preferably about 30 min to about 3 hours prior to therapy; most preferably about 1 hour before hyperthermia therapy. The dose of NO scavenger or NO synthase inhibitor to be administered are generally about the same as the dose administered to enhance hypoxic or acidic cytotoxin chemotherapy.

In a preferred aspect of the invention, an NO scavenger or NO synthase inhibitor is administered in conjunction with hyperthermia therapy and hypoxic or acidic cytotoxin chemotherapy. The NO scavenger or NO synthase inhibitor is preferably administered so that blood flow reduction and vascular stasis occurs after infusion of the cytotoxin in the tumor, and before application of hyperthermia therapy so that hypoxia and acidosis of the tumor can occur or increase. It is believed that such an approach is particularly effective, and provides an increased chance of a favorable therapeutic outcome.

When an NO synthase inhibitor is used, it is optionally followed by the administration of an NO synthase substrate, so as to promote the restoration of normal blood flow in normal tissue.

5.3.4. Solid Tumors

The present invention is directed to the use of an inhibitor of NO activity, such as a nitric oxide scavenger or an NO synthase inhibitor, as an antitumor therapy to reduce tumor blood flow and oxygenation or as an adjunct therapy to enhance the effectiveness of hypoxic or acidic cytotoxins, and of hyperthermia, against tumors, particularly hypoxic or acidic tumors. The present invention further contemplates effecting therapeutic treatment of aerobic tumors, which are normally resistant to hypoxic or acidic cytotoxins, by decreasing blood flow in such tumors and thereby increasing the sensitivity of such tumors to hypoxic or acidic cytotoxins. In a specific embodiment, the invention further contemplates achieving selective blood flow reduction in tumor tissue by administering an NO synthase inhibitor, followed by administration of an NO synthase substrate.

Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In another embodiment, dysproliferative changes (such as metaplasias and dysplasias) are treated or prevented in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology,* 2d Ed., W.B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, *Medicine,* 2d Ed., J. B. Lippincott Co., Philadelphia.

The present invention is also directed to treatment of non-malignant tumors and other disorders involving inappropriate tissue vascularization by administering a therapeutically effective amount of an inhibitor of NO activity, such as an NO scavenger or an NO synthase inhibitor, as an adjunct (additional therapy) to treatment of a disorder that involves inappropriate tissue vascularization. Inappropriate tissue vascularization includes an increase in the number of blood vessels or hypertrophy, which is an increase in the size of the blood vessels. A therapeutically effective amount of an NO scavenger or an NO synthase inhibitor is an amount effective to induce resolution of symptoms. In another aspect, a therapeutically effective amount is an amount effective to decrease blood flow through the tissue.

For example, it is contemplated that the invention is useful for the treatment of arteriovenous (AV) malformations, particularly in intracranial sites. Radiation therapy is commonly used to treat such inoperable lesions. Use of NO scavengers and/or NO synthase inhibitors could lead to enhanced rate or frequency of sclerosis or thrombus formation within these lesions and reduction in size of the malformation as detected by angiography, thereby increasing the efficacy of the approach. Reducing the time for the therapeutic effect to occur reduces the time that the patient is at continued risk for intracranial hemorrhage. In this case, use of conformal radiation treatment planning leads to preferential therapeutic effect within the volume of the AV malformation.

Hyperthermia has been used to treat psoriasis, a dermatologic condition that is characterized by inflammation and vascular proliferation. Administration of a NO scavenger or NO synthase inhibitor may be used to increase the efficacy of this therapy, by enhancing the rate of thrombosis within the effected vessels, and preferably to induce disappearance of the lesion. Similarly, hyperthermia is also being used for treatment of benign prostatic hypertrophy. This condition is also associated with inflammation and possibly vascular proliferation. Administration of an NO scavenger or an NO synthase inhibitor can enhance the therapeutic benefits of this treatment. Hyperthermia has also been used for the treatment of cutaneous fungal infections. Administration of an NO scavenger or an NO synthase inhibitor can enhance the therapeutic benefits of this treatment, and preferably induce disappearance of the lesions.

Treatment of other hyperproliferative disorders is also contemplated.

5.3.5. Irreversible Reduction in Tumor Perfusion

According to one aspect of the invention, NO synthase inhibition followed by administration of L-arginine or other NO synthase substrate provides a means of achieving the therapeutic goal of selective tumor hypoxia. For example, a NO synthase inhibitor (a competitive inhibitor, e.g., a substrate analog) can be administered to a subject having a solid tumor, followed by the administration of an NO synthase substrate, in order to achieve selective reduction in tumor blood flow and oxygenation.

In a specific embodiment, a NO synthase inhibitor can be administered concurrent with or following administration of a hypoxic or acidotic sensitizer or hyperthermia. This strategy is used to reduce tumor blood flow, increase hypoxic cell fraction, and improve retention of the drug within the tumor. Normal tissue blood flow can subsequently be restored (or at least increased toward normal levels) by the administration of L-arginine or other NO synthase substrate, thus reducing toxicity to normal tissue, while not compromising the therapeutic efficacy in the tumor. The combination of an NO synthase inhibitor followed by L-arginine or other NO synthase substrate can also be used to increase tumor retention of other chemotherapeutic agents by reducing washout, as well as to reduce thermal washout during hyperthermic therapy of tumors.

The invention can be better understood by referring to the following examples, which are provided merely by way of exemplification and is not intended to limit the invention.

6. PHARMACOLOGICAL REDUCTION OF TUMOR PERFUSION: A MECHANISM TO IMPROVE THERAPEUTIC EFFECTIVENESS OF BIOREDUCTIVE CHEMOTHERAPEUTIC AGENTS AND HYPERTHERMIA

6.1. Methods

6.1.1. General Experimental Procedure

Fischer 344 rats, weighing 150–200 g and bearing dorsal skinfold window chambers containing 8 to 10 day R3230AC (rat mammary adenocarcinoma) tumors, were anesthetized with sodium pentobarbital (40 mg/kg, intraperitoneal (IP)). The femoral artery and vein were cannulated for measurement of arterial blood pressure and intravenous (IV) infusion of drugs. The rats were mounted on the stage of a Zeiss photomicroscope II equipped with both transmitted light and epifluorescence capability. Selected vessels in the tumor center, peripheral tumor, and in normal areas of the window preparation were observed through either a black and white video camera or a silicon intensified tube camera and videotaped using a Super VHS recorder. The same vessels were observed both prior to treatment (baseline) and following treatments, as described below.

6.1.2. NO Synthase Inhibition Experiments

In experiments investigating the effect of NO synthase inhibition on tumor blood flow, the dorsal glass window was removed from the window chamber and Earle's Balanced Salt Solution (BSS), heated to 36° C. and gassed with 95% $N_2$/5% $CO_2$, was superfused across the window preparation. Following baseline video recordings of blood flow, $N^G$-monomethyl-L-arginine (L-NMA, Calbiochem cat # 475886; 50 and 100 µM in Earle's BSS, at 36° C., bubbled with 95% $N_2$/5% $CO_2$) was superfused at 1.5–2 ml/min across the exposed face of the tumor for at least 45 min before video recordings of the same vessels were made.

In a separate set of experiments, the NO synthase inhibitor L-NMA was administered IV at 3.0 mg/kg (Kilbourne et al., 1990, Proc. Natl. Acad. Sci. USA 87:3629–3632) and mean arterial pressure, heart rate, and tumor and normal vessel blood flows were monitored.

6.1.3. NO Scavenging Experiments

In experiments investigating the effect of NO scavenging on tumor blood flow, cell-free hemoglobin (CFHb, bovine origin, Biopure Formula 1; 0.1 g/kg) was infused IV. This dose represents less than 5% of the total blood volume of a 150 rat. Again, baseline arterial pressure, heart rates, and video recordings of vessel blood flow were made prior to treatment with CFHb (baseline) and following treatment.

6.1.4. NO Scavenging—Hypoxic Sensitizer Experiments

Experiments investigating the effect of NO scavenging combined with a hypoxic cell cytotoxin on tumor growth were performed. Human rhabdomyosarcoma xenographs (DU-217P) were implanted in nude mice. CFHb (Biopure Formula 1, 0.1 g/kg) was administered IV 60 min following administration of mitomycin C (15.7 mg/m$^2$) and the delay in tumor growth was determined. A Wilcoxon rank sum test was used to compare treatments with controls. A p value $\leq 0.05$ was considered significant.

6.2. Results

6.2.1. NO Synthase Experiments Superfusion

Administration of L-NMA via a superfusion medium just to the window chamber surface did not change systemic cardiovascular function, as indicated by observed changes in mean arteriolar pressure (MAP). Average baseline MAP was 105 mm Hg, and average MAP during L-NMA superfusion was 101 mm Hg. Table 1 summarizes the results of 4 superfusion experiments on tumor and normal vessel blood flow:

TABLE 1

Effect of L-NMA Superfusion on Tumor and Normal Vessel Blood Flow

| Vessel Location | Blood Flow | |
| --- | --- | --- |
| | Baseline | L-NMA Superfusion |
| Tumor<br>N = 7 | Flow present<br>7/7 vessels | No Flow 3/7<br>Greatly Reduced 2/7<br>Reduced 1/7<br>Flow not changed 1/7 |
| Normal<br>N = 8 | Flow present<br>8/8 | No Flow 1/8<br>Flow not changed 7/8 |

6.2.2. NO Synthase Inhibition Experiments Intravenous Administration

Intravenous administration of L-NMA caused a transient 20 mm Hg increase in MAP, peaking at 5 min following administration and returning to preinjection levels by 30 min, with little or no change in heart rate (FIG. 1). Table 2 summarizes the results of 2 intravenous L-NMA administration experiments on tumor vessel blood flow:

TABLE 2

Effect of Intravenous L-NMA on Tumor Vessel Blood Flow

| Vessel Location | Baseline | Intravenous L-NMA |
| --- | --- | --- |
| Tumor<br>N = 24 | Flow present<br>24/24 | No Flow 4/24<br>Greatly Reduced 5/24<br>Reduced 4/24<br>Flow not changed 11/24 |
| Normal<br>None observed | | |

6.2.3. NO Scavenging Experiments

Intravenous administration of CFHb caused a transient 35 mm Hg increase in average MAP, accompanied by a baroreflex-induced decrease in heart rate, from 256 beats/min to 243 beats/min (FIG. 2). Although MAP returned to preinjection levels by 60 min following CFHb injection, heart rate remained decreased, with some indication of a trend towards preinjection levels. Table 3 summarizes the results of experiments with intravenously administered CFHb on tumor and normal vessel blood flow. Significantly, administration of L-arginine (100 mg/kg IV) did not reverse the CFHb-induced reduction in tumor vessel blood flow.

TABLE 3

Effect of Intravenous CFHb Administration on Normal and Tumor Vessel Blood Flow

| Vessel Location | Baseline | CFHb Treatment |
|---|---|---|
| Tumor<br>N = 28 | Flow present<br>28/28 | No Flow (9/28)<br>Greatly Reduced (7/28)<br>Slightly Reduced (1/28)<br>Flow not changed (11/28) |
| Normal<br>N = 4 | Flow present<br>4/4 | Flow reduced 1/4<br>Flow not changed (3/4) |

6.2.4. NO Scavenging—Hypoxic Sensitizer Experiments

The results of experiments designed to show the effects of an NO scavenger on hypoxic cytotoxin sensitization are shown in Table 4. Mitomycin C treatment alone resulted in a 6 day delay in tumor growth compared with the control (no treatment) group (p<0.001). CFHb treatment alone resulted in no significant delay of tumor growth compared with the control group (p=0.342). The combination of CFHb and mitomycin C resulted in a 10 day delay in tumor growth compared with the control group (p<0.001). The data clearly show a trend toward increased enhancement in growth delay with the combination of CFHb and mitomycin C compared with mitomycin C alone (4.4 days; p=0.09).

TABLE 4

Effect of CFHb and Mitomycin C on Growth Delay of DU-217P Human Rhabdosarcoma Xenographs

| Treatment | Mitomycin C vs Control | CFHb vs Control | Mitomycin and CF vs Control | Mitomycin and CFHb vs Mitomycin |
|---|---|---|---|---|
| Regressions | 1/10 | 0/10 | 3/10 | N/A |
| Δ Treatment-Control (days) | 6.03 days | 1.16 days | 10.36 days | 4.4 days |
| P value ≦ | 0.001 | 0.342 | 0.001 | 0.09 |

6.3. Conclusions

In summary, a series of 11 experiments on the effect of NO inhibition on tumor blood flow have been performed, which included 59 tumor vessels and 12 normal tissue vessels. Modulation of NO levels with the NO synthase inhibitor L-NMA or the NO scavenger CFHb resulted in decreased blood flow in 61% of the tumor vessels studied, compared with decreased blood flow in 17% of the blood vessels in normal tissues. Complete vascular stasis resulting from administration of either the NO synthase inhibitor or the NO scavenger was observed in 27% of all tumor vessels and 8.3% of normal tissue vessels. Thus, the effects of administration of the NO synthase inhibitor or the NO scavenger appear to occur preferentially, though not exclusively, in tumor tissues.

L-NMA or CFHb-induced vascular stasis in tumor vessels could not be reversed with L-arginine. This result suggests that the effect of NO reduction may involve more than vasomotor tone in tumor. For example, platelet adhesion may be playing a role.

The combination of the NO scavenger CFHb with the hypoxic cytotoxin mitomycin C demonstrates a clear increase in tumor growth delay compared to mitomycin C alone, although the increase in not statistically significant at this time using the Wilcoxon rank sum analysis.

7. EXAMPLE: CHANGES IN TISSUE AND TUMOR OXYGENATION WITH ADMINISTRATION OF STROMA FREE HEMOGLOBINS

This Example is a report of physiological studies on the effect of administration of stroma free hemoglobins on normal tissue and tumor oxygenation. The results are based on three animals per experimental group.

7.1. Materials and Methods

The three experimental groups were (1) p50 of 9.0 mmHg, (2) p50 of 32.0 mm Hg and (3) Albumin. The concentration of all three solutions at the time of administration was 10 g per 100 ml. The dose was 1.5 ml/125 gm body weight administered as a slow infusion over 10 minutes. All animals had a femoral arterial catheter placed for continuous monitoring of arterial pressure. Heart rates were also obtained from the pressure tracings. Clark style microelectrodes were placed in muscle and in two R3230AC tumor sites for monitoring of tissue oxygenation after administration of the various solutions. The R3230AC tumor is a rat mammary adenocarcinoma (see Section 6.1.1., supra). The tumor was transplanted into the animal's leg.

All the animals were anesthetized with phenobarbital prior to the experiments. Body temperature was maintained with at 37° C. with a thermostatically controlled heating blanket.

7.2. Results

The changes in systemic cardiovascular function are noted in FIG. 3. For all three infusion solutions a mild tachycardia was noted, which was most prominent for albumin. The tachycardia persisted out to 60 minutes after the initiation of the experiment (FIG. 3). There was no difference in the systolic-diastolic pressure difference for any of the infusion solutions over the 60 minute sampling interval. This could be interpreted as reflecting no change in stroke volume. There was a mild decrease in mean arterial pressure from baseline (100 mmHg) to an average reading of approximately 85 to 90 mm Hg after infusion of the albumin solution. We have observed this type of reaction previously with Fluosol and Ringers solutions, and have attributed it to a baroreceptor reflex. In contrast, the mean arterial pressures for both hemoglobin solutions increased following administration (FIG. 4). These effects persisted out to 60 minutes after administration. Thus, the hemoglobin solutions appear to be offsetting the baroreceptor reflex. This may be due to the nitric oxide scavenging availability of the hemoglobin solutions, which is absent from the albumin solution. All three solutions created hemodilution as was reflected by a drop in hemocrit. The hemocrit appeared to be fairly stable once the infusion was completed, thus indicating that the solutions were isotonic nature (FIG. 5).

Changes in tissue and tumor oxygen tension during and after the infusion of these solutions are noted in FIGS. 6–9.

The administration of albumin did not seem to effect muscle $pO_2$ at all (FIG. 6). In contrast to the results observed in muscle, the administration of albumin appeared to improve tumor oxygenation shortly after completion of solution administration (FIG. 7). This result may be simply due to hemodilution affects which may improve tumor blood flow via an effect on blood rheology. By comparison both hemoglobin solutions created a drop in tumor oxygenation. Interestingly, the most prominent drop occurred after administration of the 32 mm Hg hemoglobin (FIGS. 7, 8, and 9). Hemoglobin did not significantly affect muscle oxygenation.

7.3. Discussion

The drop in tumor oxygenation that results from administration of hemoglobin has clear therapeutic implications in strategies to selectively kill hypoxic cells. Hemoglobin did not induce a significant drop in muscle oxygenation, however, thus administration of stroma free hemoglobin selectively affects tumor tissue oxygenation, but not normal tissue. The selective nature of the hemoglobin induced decrease in oxygenation enhances its value as an adjuvant in hypoxic tumor therapy.

Stroma free hemoglobin scavenges nitric oxide, as shown by its ability to offset the baroreceptor reflex. NO scavenging is believed to cause the observed drop in tumor oxygenation as well.

8. SELECTIVE REDUCTION OF TUMOR PERFUSION WITH NITRIC OXIDE SYNTHASE INHIBITION

As described herein, we have found that pharmacological inhibition of vascular NO followed by L-arginine results in selective and irreversible tumor flow reduction and that normal tissue flow, but not tumor flow, can be subsequently restored by the administration of L-arginine. The microvascular effects of 60 min superfusion of the nonspecific NO synthase inhibitor, $N^G$ monomethyl L-arginine (L-NMA, 50 $\mu$M), followed by 60 min superfusion of the true substrate for NO production, L-arginine (200 $\mu$M), were determined using video microscopy in female Fisher 344 rats implanted with dorsal skin flap window chambers and R3230Ac mammary adenocarcinomas. L-NMA decreased tumor preparation blood flow 43% and control preparation blood flow 83% through reduction of venule diameter and red blood cell (RBC) velocity, decreased microvascular length density, and increased the percentage of tumor vessels showing intermittent vascular flow and stasis. Although these changes were reversible with L-arginine in control venules, tumor venule diameter, RBC velocity, and vessel length density were not restored.

8.1. Materials and Methods

8.1.1. Animal Model

Female Fischer 344 rats (Charles River Laboratories, Raleigh, N.C.), weighing 150–200 g, were surgically implanted with cutaneous window chambers in order to visualize granulating subcutaneous tissue microvasculature and to provide a substrate for tumor growth. Details of chamber design and surgical technique have been published elsewhere (Pappenfus et al., 1979, Microvasc. Res. 18:311–318). Briefly, aseptic surgical dissection of a 1.0 cm diameter hole was made through opposing surfaces of the dorsal skin flap, leaving a single fascial plane with two or three artery-vein pairs. In tumor-bearing preparations, a 0.1 $mm^3$ piece of tumor (R3230Ac mammary adenocarcinoma (Hilf et al., 1965, Cancer Res. 25:286–299) was placed onto the fascial plane at the time of surgery, whereas in control chambers, no tumor was implanted. Following surgical implantation, animals were housed individually in an environmental chamber maintained at 34° C. and 50% humidity with continuous access to food and water. All preparations were used 9–11 days following surgery, at which time the tumors were 3–4 mm in diameter.

8.1.2. Measurement of Venule Intraluminal Diameter and RBC Velocity

Measurements of venule diameter and RBC velocity were performed using video microscopy of the window chamber preparation as it was transilluminated with a 40 W tungsten source at 200× on a Zeiss photomicroscope microscope stage (Carl Zeiss, Photomicroscope III, New York, N.Y.) equipped with a two axis linear measuring system (2-LM.5, Boeckeler Instruments, Tucson, Ariz.). Images were captured with a video camera (MTI CCD-72, Dage-MTI, Michigan City, Mich.) and recorded on S-VHS tape for later analysis of vessel diameter (SVO-9500MD, Sony Corporation of America, San Jose, Calif.). Identities and locations of individual vessels and exact location of RBC velocity measurement were noted by tracing the vascular bed for each region of interest onto acetate sheets placed over the video monitor and by noting the x–y position of the field. Vessel diameter was measured at sites of RBC velocity measurement by using a frame grabber (PC Vision+, Imaging Technology Inc., Woburn, Mass.) and image analysis software (Java, Jandel Scientific, Conte Madera, Calif.). The dual window technique was used to measure RBC velocity (IPM Model 204 Video Analyzer and 102B Velocity Tracker, San Diego, Calif.) (Tompkins et al., 1974, Rev. Sci. Instrum. 45:647–649). Superimposition of a videotimer signal (CTG-55 Video Timer, For.A Co., Ltd., Los Angeles, Calif.) was used to document time of the videotape record relative to treatment. Relative flow was derived to illustrate the interaction between cross sectional area and velocity, where:

Relative Flow=(fractional change in diameter)$^{2}$*(fractional change in RBC velocity)

8.1.3. Determination of Vessel Length Density and Intermittent Flow Ratio

Videotaped segments of each experiment prior to treatment (baseline), following treatment with L-NMA, and again following treatment with L-arginine were used to obtain the morphometric index vessel length-density (Chen et al., 1981, Am. J. Physiol. 241:H306–H310), and frequency of intermittent vascular flow and stasis. For determination of vessel length density, a square grid was superimposed over the video screen and the number of intersections between the grid and all vessels with RBC flow during a 1 min period were counted. The number of grid squares per video field was 408. Typically the number of intersections ranged from 150 to 300 per video field. The vessel length-density in $mm/mm^3$ tissue was calculated using:

Length Density=$N_{intersections}/(4gtd)$, where $N_{intersections}$=number of intersections between vessels and gridlines, g=number of blocks in grid (408), d=length of one grid square side corrected for magnification (0.0193 mm), and t=measured depth of field through which microvessels could be discerned (0.15 mm). The change in vessel length density with treatment was determined by dividing treatment length density by baseline length density.

Percent of venules demonstrating intermittent flow or stasis, where intermittent flow was defined as stopped or reversed flow for ≧5 sec, was also determined from the videotaped experiments. First, the total number of vessels per field was counted. A vessel was defined as a segment between branch points. Vessels showing intermittent flow or stasis were counted. Vessels which could not be positively identified as having flow were noted separately. The percent of vessels demonstrating intermittent flow or stasis was calculated as the number of vessels with intermittent flow and flow stasis observed at any time during the 1 min observation interval divided by the total number of vessels in the field minus the number of vessels with undetermined flow status. Each vessel with intermittent flow was counted only once, even if it stopped more than once during the 1 min interval. The percent of venules demonstrating intermittent flow or stasis was determined for both L-NMA and L-arginine treatment.

8.1.4. Experimental Protocol

The animals were anesthetized with sodium pentobarbital (40 mg/kg, i.p.) and kept on a thermostatically controlled blanket at a rectal temperature of 37 C (Model 50-7503 Homeothermic Blanket, Harvard Bioscience, S. Natick, Mass.). The femoral artery and vein were cannulated for measurement of arterial blood pressure and i.v. infusion of drugs. Arterial pressure waveforms (Gould P23XL, Gould Instrument Systems, Cleveland, Ohio) and RBC velocity were each digitized at 200 Hz and recorded to disk for later analysis, with heart rate and mean arterial pressure determined from the pulsatile arterial waveform (AT-Codas, Data Instruments, Akron, Ohio). Rats were placed in lateral recumbency on the microscope stage and the upper window was removed. EBSS (Gibco cat # 450-1100EB, Life Technologies Inc., Grand Island, N.Y.) bubbled with 95% $N_2$/5% $CO_2$, was superfused across the surface at 1–2 ml/min. Temperature of the medium at the tissue surface was 32° C.

Selected fields of venules were observed in the tumor center, the hypervascular tumor periphery, and in surrounding "normal" areas of granulating or healing subcutaneous tissue away from the tumor. Postcapillary venules in granulating tissue were examined in nontumor-bearing control window chambers, as well. The same vessels were observed prior to treatment and following treatment. Following pretreatment observations, 50 μM L-NMA (Calbiochem cat # 475886; in EBSS) was superfused across the exposed face of the tumor for 60 min and measurements were repeated. L-arginine, (Calbiochem cat # 1820; in EBSS), 200 μM, was then superfused across the chamber for an additional 60 min before measurements of the same vessels were again made.

8.1.5. Statistical Analysis

Relative changes from baseline diameter, RBC velocity, mean arterial pressure, and heart rate for control and tumor-bearing preparations were assessed using a mixed-effects linear model (Crowder, M. J., Hand, D. J. *Analysis of Repeated Measures*, London: Chapman and Hall, 1990). This model accounts for multiple measurements on each animal by utilizing within-animal and between-animal sources of variation in the analysis. Means and standard errors (and 95% confidence intervals) were estimated from the models, which were fit using the SAS/STAT procedure PROC MIXED (SAS Institute, Inc. SAS Technical Report P-229, SAS/STAT Software: Changes and Enhancements, Release 6.07. Cary, N.C.: SAS Institute, Inc., 1992). All statistical tests of significance were based on 2-sided tests and a significance level of 0.05.

8.2. Results

8.2.1. Baseline Parameters

Pretreatment diameter and RBC velocity (mean and standard error [SEM]) for control (n=3) and tumor-bearing (n=15) window chamber experiments are summarized in Table 5. There were no pairwise differences in mean diameter or mean RBC velocity between the three categories of tumor vessels, adjusted for multiple comparisons. Pretreatment diameter and RBC velocity for normal venules in tumor chambers were similar to those of control chamber venules. Superfusion of L-NMA and L-arginine had no effect on relative change in mean arterial blood pressure and heart rate (Table 6).

TABLE 5

Baseline Postcapillary Venular Blood Flow Parameters

| Venule Type | Chamber | Number of Animals | Number of Vessels | Mean Diameter (SEM μm) | Mean Velocity (SEM mm/sec) |
|---|---|---|---|---|---|
| Central Tumor | Tumor | 8 | 39 | 32.2 (13.2) | 0.55 (0.19) |
| Peripheral Tumor | Tumor | 7 | 39 | 22.0 (4.2) | 0.56 (0.28) |
| Normal, near Tumor | Tumor | 6 | 36 | 34.7 (4.6) | 0.32 (0.09) |
| Normal, no Tumor | Control | 3 | 37 | 25.5 (18.5) | 0.35 (0.37) |

There were no significant pairwise differences (where p<0.05, adjusted for multiple comparisons) in mean diameter or mean velocity between vessels. Tumor-bearing chamber normal vessels were not significantly different from control chamber normal vessels.

TABLE 6

Relative Changes in Mean Arterial Pressure and Heart Rate After Superfusion of L-NMA and L-arginine

| Vessel | Chamber | L-NMA Mean Arterial Blood Pressure Change (95% CI) | L-arginine Mean Arterial Blood Pressure Change (95% CI) |
|---|---|---|---|
| Central Tumor | Tumor | 0.95 (0.90–1.00) | 0.93 (0.81–1.06) |
| Peripheral Tumor | Tumor | 0.98 (0.94–1.03) | 0.97 (0.85–1.09) |
| Normal, near Tumor | Tumor | 0.96 (0.91–1.00) | 0.89 (0.77–1.02) |
| Normal, no Tumor | Control | 0.97 (0.88–1.07) | 0.97 (0.75–1.19) |

| Vessel | Chamber | L-NMA Heart Rate Change (95% CI) | L-arginine Heart Rate Change (95% CI) |
|---|---|---|---|
| Central Tumor | Tumor | 0.89 (0.83–0.95) | 0.93 (0.88–0.99) |
| Peripheral Tumor | Tumor | 0.97 (0.85–0.98) | 0.96 (0.90–1.02) |
| Normal, near Tumor | Tumor | 0.96 (0.89–1.02) | 0.89 (0.84–0.95) |
| Normal, no Tumor | Control | 0.90 (0.78–1.03) | 0.92 (0.83–1.02) |

There were no significant differences in mean arterial pressure or heart rate between treatment, vessel type, or tumor and control preparations.

8.2.2. Vessel Diameter

Superfusion of L-NMA significantly reduced baseline diameter for all types of tumor preparation venules as well as venules in non-tumor control preparations (FIG. 10; all p<0.05). There were no significant pairwise differences between individual vessel types with respect to relative diameter changes following L-NMA. However, there was a greater reduction in vessel diameter in non-tumor than tumor bearing preparations (p=0.02). Superfusion of L-arginine had a negligible effect in restoring venule diameters toward baseline in tumor preparations. Venules in control preparations, however, returned to pretreatment diameter following L-arginine. There were no significant pairwise differences between tumor preparation vessels with respect to relative change in diameter following L-arginine. There was, however, a significant difference in venule diameter between tumor and control window preparations following L-arginine (p=0.01).

8.2.3. RBC Velocity

Both normal control venules and central tumor venules showed significant reductions from pretreatment RBC velocity following L-NMA (FIG. 11; both p<0.05). Compared with normal venules near the tumor, RBC velocities for tumor center venules and peripheral tumor venules were both significantly reduced following L-NMA (p<0.001, p=0.005, respectively). L-NMA caused a significantly greater reduction in RBC velocity in control preparations as compared with tumor-bearing preparations (p=0.004). L-arginine returned RBC velocity toward pretreatment levels in control preparations, and restored RBC velocity in both peripheral tumor venules and normal venules near the tumor. RBC velocity in central tumor venules, however, was further reduced from baseline following L-arginine (p<0.05). Central tumor venule RBC velocity remained significantly lower following L-arginine than that of both peripheral tumor venules and normal venules near the tumor (p=0.05, and p=0.03, respectively).

8.2.4. Venule Flow

Superfusion with L-NMA reduced flow by 43% in both central tumor and peripheral tumor venules, and reduced flow by 17% in normal venules near tumors, while non-tumor control venule flow was reduced by 83% (FIG. 12). L-arginine increased non-tumor control venule flow, peripheral tumor venule flow, and flow in normal venules near tumors to nearly 65% of their pretreatment values. Flow in central tumor venules, however, decreased to 48% of baseline in the presence of L-arginine. To avoid multiplication of error inherent in the determination of both diameter and RBC velocity, statistical analysis was not performed on relative flow data.

8.2.5. Vessel Length Density

Although not statistically significant, tumor preparations showed a tendency toward reduction in vessel length density relative to baseline with L-NMA treatment (FIG. 13; where p=0.07 for central tumor venules, and p=0.08 for both peripheral tumor venules and normal venules near tumors). Vessel length density further decreased relative to baseline following L-arginine for both tumor center and peripheral tumor vessels (p=0.01 and p=0.05, respectively).

8.2.6. Intermittent Vascular Flow and Stasis

Superfusion with L-NMA increased intermittent vascular flow and stasis in central tumor vessels relative to baseline (FIG. 14; p=0.03). Intermittent vascular flow and stasis showed a tendency toward an increase in peripheral tumor venules and in normal venules near tumors, as well (p=0.06 for both comparisons). Treatment with L-arginine returned intermittent vascular flow and stasis toward pretreatment levels for all vessel types.

8.3. Conclusions

We have shown that NO synthase inhibition results in selective and irreversible tumor flow reduction and that normal tissue flow, but not tumor flow, can be subsequently restored by L-arginine.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A method for treating an animal having a disorder involving inappropriate tissue vascularization comprising administering a therapeutically effective amount of a nitric oxide scavenger as an adjunct to treatment of the disorder.

2. The method according to claim 1 in which the nitric oxide scavenger is cell free hemoglobin.

3. The method according to claim 1 in which the animal is a human.

4. The method according to claim 1 in which the treatment of the disorder is hyperthermia therapy.

5. A method for treating an animal having a disorder involving inappropriate tissue vascularization comprising administering a therapeutically effective amount of a nitric oxide synthase inhibitor as an adjunct to treatment of the disorder.

6. The method according to claim 5 in which the nitric oxide synthase inhibitor is a substituted L-arginine.

7. The method according to claim 5 in which the animal is a human.

8. The method according to claim 5 in which the treatment of the disorder is hyperthermia therapy.

* * * * *